(12) United States Patent
Schraga

(10) Patent No.: US 7,704,265 B2
(45) Date of Patent: Apr. 27, 2010

(54) DISPOSABLE/SINGLE-USE BLADE LANCET DEVICE AND METHOD

(75) Inventor: Steve Schraga, North Miami, FL (US)

(73) Assignee: Stat Medical Devices, Inc., North Miami, FL (US)

( * ) Notice: Subject to any disclaimer, the term of this patent is extended or adjusted under 35 U.S.C. 154(b) by 195 days.

(21) Appl. No.: 11/265,151

(22) Filed: Nov. 3, 2005

(65) Prior Publication Data

US 2007/0095178 A1 May 3, 2007

(51) Int. Cl.
*A61B 5/151* (2006.01)
*A61B 17/3209* (2006.01)

(52) U.S. Cl. .......................... 606/182; 30/335; 600/583

(58) Field of Classification Search ................. 606/180, 606/181, 187, 182, 22, 110, 117, 207–211; 83/130; 600/583, 573; 30/154, 155, 335
See application file for complete search history.

(56) References Cited

U.S. PATENT DOCUMENTS

| 676,678 | A | | 6/1901 | Ellifrits |
|---|---|---|---|---|
| 931,791 | A | * | 8/1909 | Niergarth .................... 606/182 |
| 1,135,465 | A | | 4/1915 | Pollock |
| 2,823,677 | A | | 2/1958 | Hein, Jr. |
| 2,848,809 | A | | 8/1958 | Crowder |
| 3,589,213 | A | | 6/1971 | Gourley |
| 3,760,809 | A | | 9/1973 | Campbell, Jr. |
| 4,064,871 | A | | 12/1977 | Reno |
| 4,139,011 | A | | 2/1979 | Benoit et al. |
| 4,157,086 | A | | 6/1979 | Maiorano et al. |
| 4,203,446 | A | | 5/1980 | Höfert et al. |

(Continued)

FOREIGN PATENT DOCUMENTS

CA 523078 3/1956

(Continued)

OTHER PUBLICATIONS

Kasper, L. "One Spring returns . . ." from "Illustrated Sourcebook of Mechanical Components" Parmley, R.O. ed. McGraw Hill © 2000, retrieved from Knovel.com on Nov. 20, 2007. pp. 16-18 through 16-21. Pertinent Portion from 16-21 is reprinted in the office action body.*

(Continued)

*Primary Examiner*—Kenneth E. Peterson
*Assistant Examiner*—Sean Michalski
(74) *Attorney, Agent, or Firm*—Greenblum & Bernstein, P.L.C.

(57) ABSTRACT

Single-use blade lancet device includes a body having a rear end and a front end. A triggering mechanism has a blade tip opening and is mounted to the body. A blade member is movably mounted within the body and includes a front end and a rear end. The blade member is movable at least between a first retracted position, an extended position, and a second retracted position. A biasing arrangement biases the blade member from the first retracted position towards the extended position and then towards the second retracted position. A guiding arrangement guides the blade member while the blade member moves from the first retracted position towards the extended position and then towards the second retracted position. This Abstract is not intended to define the invention disclosed in the specification, nor intended to limit the scope of the invention in any way.

8 Claims, 32 Drawing Sheets

U.S. PATENT DOCUMENTS

| | | |
|---|---|---|
| 4,257,561 A | 3/1981 | McKinney |
| 4,388,925 A | 6/1983 | Burns |
| 4,426,105 A | 1/1984 | Plaquin et al. |
| 4,438,770 A | 3/1984 | Unger et al. |
| 4,449,529 A | 5/1984 | Burns et al. |
| 4,469,110 A | 9/1984 | Slama |
| 4,517,978 A | 5/1985 | Levin et al. |
| 4,527,561 A | 7/1985 | Burns |
| 4,539,988 A | 9/1985 | Shirley et al. |
| 4,553,541 A | 11/1985 | Burns |
| 4,628,929 A | 12/1986 | Intengan et al. |
| 4,643,189 A | 2/1987 | Mintz |
| 4,785,858 A | 11/1988 | Valentini et al. |
| RE32,922 E | 5/1989 | Levin et al. |
| 4,834,667 A | 5/1989 | Fowler et al. |
| 4,858,607 A | 8/1989 | Jordan et al. |
| 4,869,249 A | 9/1989 | Crossman et al. |
| 4,895,147 A | 1/1990 | Bodicky et al. |
| 4,924,879 A * | 5/1990 | O'Brien .................. 600/583 |
| 4,976,724 A | 12/1990 | Nieto et al. |
| 4,990,154 A | 2/1991 | Brown et al. |
| 5,035,704 A * | 7/1991 | Lambert et al. ............ 606/182 |
| 5,074,872 A | 12/1991 | Brown et al. |
| 5,133,730 A | 7/1992 | Biro et al. |
| 5,147,375 A | 9/1992 | Sullivan et al. |
| 5,212,879 A | 5/1993 | Biro et al. |
| 5,269,799 A | 12/1993 | Daniel |
| 5,282,822 A | 2/1994 | Macors et al. |
| 5,304,193 A | 4/1994 | Zhadanov |
| 5,314,441 A * | 5/1994 | Cusack et al. ............... 606/182 |
| 5,318,584 A | 6/1994 | Lange et al. |
| 5,324,303 A | 6/1994 | Strong et al. |
| 5,350,392 A | 9/1994 | Purcell et al. |
| 5,356,420 A | 10/1994 | Czernecki et al. |
| 5,366,470 A | 11/1994 | Ramel |
| 5,395,388 A | 3/1995 | Schraga |
| 5,423,847 A | 6/1995 | Strong et al. |
| 5,439,473 A | 8/1995 | Jorgensen |
| 5,454,828 A | 10/1995 | Schraga |
| 5,464,418 A | 11/1995 | Schraga |
| 5,476,101 A | 12/1995 | Schramm et al. |
| 5,509,345 A | 4/1996 | Cyktich |
| 5,518,004 A | 5/1996 | Schraga |
| 5,527,333 A | 6/1996 | Nikkels et al. |
| 5,527,334 A | 6/1996 | Kanner et al. |
| 5,529,581 A | 6/1996 | Cusack |
| 5,545,174 A | 8/1996 | Schenk et al. |
| 5,554,166 A | 9/1996 | Lange et al. |
| 5,569,286 A | 10/1996 | Peckham et al. |
| 5,569,287 A | 10/1996 | Tezuka et al. |
| 5,571,132 A | 11/1996 | Mawhirt et al. |
| D376,203 S | 12/1996 | Schraga |
| 5,613,978 A | 3/1997 | Harding |
| 5,628,764 A | 5/1997 | Schraga |
| 5,628,765 A | 5/1997 | Morita |
| 5,643,306 A | 7/1997 | Schraga |
| 5,662,672 A | 9/1997 | Pambianchi et al. |
| 5,730,753 A | 3/1998 | Morita |
| 5,733,300 A | 3/1998 | Pambianchi et al. |
| 5,741,288 A | 4/1998 | Rife |
| RE35,803 E | 5/1998 | Lange et al. |
| 5,772,677 A | 6/1998 | Mawhirt et al. |
| 5,797,940 A | 8/1998 | Mawhirt et al. |
| 5,797,942 A | 8/1998 | Schraga |
| 5,873,887 A | 2/1999 | King et al. |
| 5,879,367 A | 3/1999 | Latterell et al. |
| 5,908,434 A | 6/1999 | Schraga |
| 5,916,230 A | 6/1999 | Brenneman et al. |
| 5,951,582 A | 9/1999 | Thorne et al. |
| 5,984,940 A | 11/1999 | Davis et al. |
| 6,010,519 A | 1/2000 | Mawhirt et al. |
| 6,022,366 A | 2/2000 | Schraga |
| 6,042,595 A | 3/2000 | Morita |
| 6,045,567 A | 4/2000 | Taylor et al. |
| 6,056,765 A | 5/2000 | Bajaj et al. |
| 6,071,294 A | 6/2000 | Simons et al. |
| D428,150 S | 7/2000 | Ruf et al. |
| 6,136,013 A | 10/2000 | Marshall et al. |
| 6,152,942 A | 11/2000 | Brenneman et al. |
| 6,156,050 A | 12/2000 | Davis et al. |
| 6,156,051 A | 12/2000 | Schraga |
| 6,168,606 B1 | 1/2001 | Levin et al. |
| 6,183,489 B1 | 2/2001 | Douglas et al. |
| 6,190,398 B1 | 2/2001 | Schraga |
| 6,192,891 B1 | 2/2001 | Gravel et al. |
| 6,197,040 B1 | 3/2001 | Le Vaughn et al. |
| 6,210,420 B1 | 4/2001 | Mauze et al. |
| 6,221,089 B1 * | 4/2001 | Mawhirt .................. 606/181 |
| 6,228,100 B1 | 5/2001 | Schraga |
| 6,258,112 B1 | 7/2001 | Schraga |
| 6,283,982 B1 | 9/2001 | Le Vaughn et al. |
| 6,306,152 B1 | 10/2001 | Verdonk et al. |
| 6,322,574 B1 | 11/2001 | Lloyd et al. |
| 6,322,575 B1 | 11/2001 | Schraga |
| 6,332,871 B1 | 12/2001 | Douglas et al. |
| 6,346,114 B1 | 2/2002 | Schraga |
| 6,358,265 B1 | 3/2002 | Thorne, Jr. et al. |
| 6,364,889 B1 | 4/2002 | Kheiri et al. |
| 6,379,317 B1 | 4/2002 | Kintzig et al. |
| 6,395,495 B1 | 5/2002 | Montagnier et al. |
| 6,409,740 B1 | 6/2002 | Kuhr et al. |
| 6,419,661 B1 | 7/2002 | Kuhr et al. |
| 6,451,040 B1 | 9/2002 | Purcell |
| 6,464,649 B1 | 10/2002 | Duchon et al. |
| 6,506,168 B1 | 1/2003 | Fathallah et al. |
| 6,514,270 B1 | 2/2003 | Schraga |
| 6,540,762 B1 | 4/2003 | Bertling |
| 6,558,402 B1 | 5/2003 | Chelak et al. |
| 6,929,649 B2 * | 8/2005 | Pugh ..................... 606/182 |
| 2003/0199912 A1 * | 10/2003 | Pugh ..................... 606/182 |
| 2004/0236362 A1 | 11/2004 | Shraga |
| 2005/0125018 A1 | 6/2005 | Galloway et al. |
| 2006/0106411 A1 | 5/2006 | Schraga |

FOREIGN PATENT DOCUMENTS

| | | |
|---|---|---|
| EP | 0061102 | 9/1982 |
| EP | 0137975 | 4/1985 |
| EP | 0189117 | 7/1986 |
| EP | 0885590 | 12/1998 |
| EP | 0904731 | 3/1999 |
| EP | 1074219 | 2/2001 |
| FR | 1126718 | 11/1956 |
| GB | 1521411 | 8/1978 |

OTHER PUBLICATIONS

Sutor et al., ABleeding from Standardized Skin Punctures: Automated Technic for Recording Time, Intensity, and Pattern of Bleeding@, *A.J.C.P.*, vol. 55, pp. 541-549 (May 1971).

U.S. Appl. No. 11/052,738 in the name of Schraga entitled "A Single Use Lancet Device", filed Feb. 7, 2005.

U.S. Appl. No. 10/988,636 in the name of Schraga entitled "Single-Use Blade Lancet Device", filed Nov. 16, 2004.

* cited by examiner

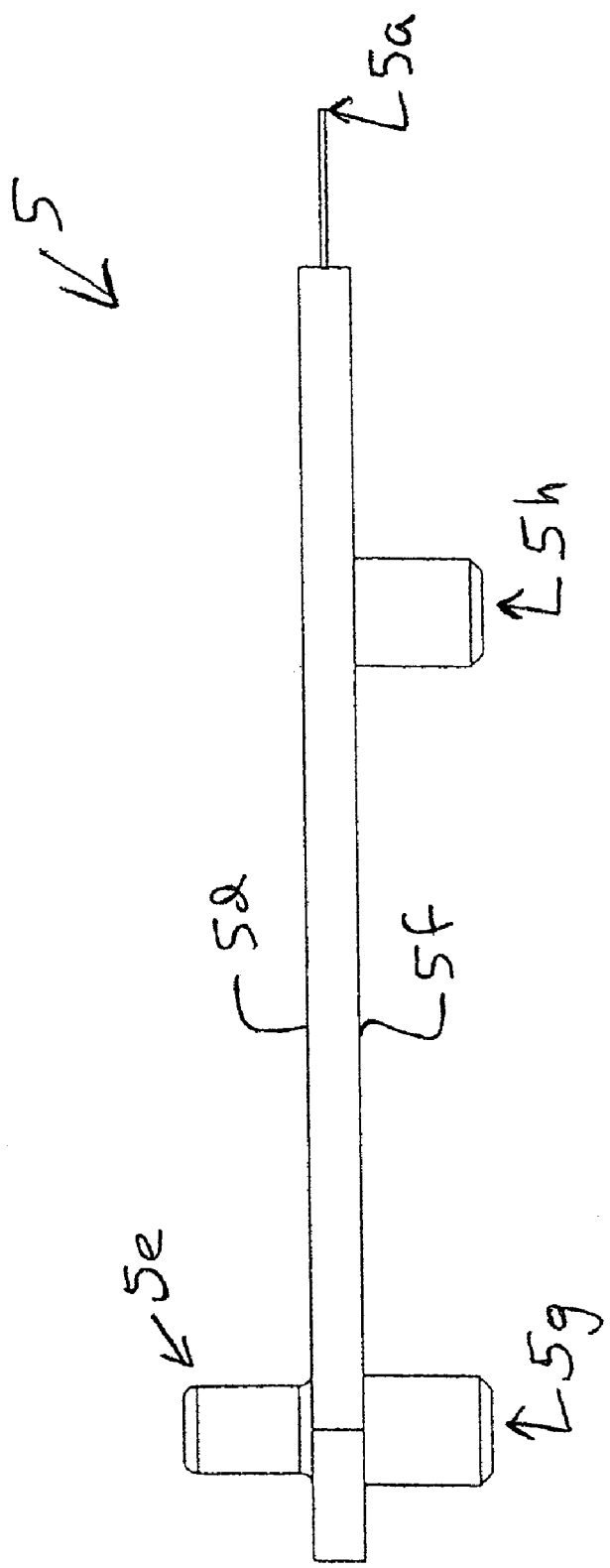

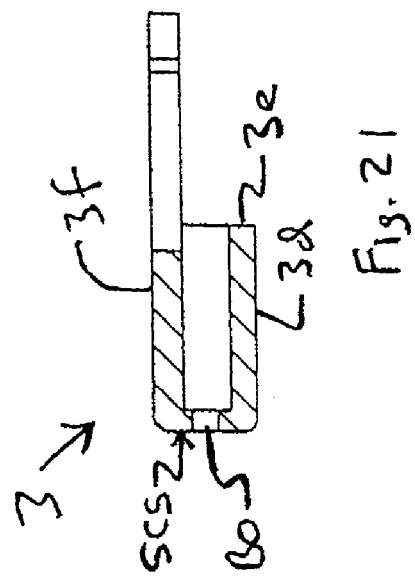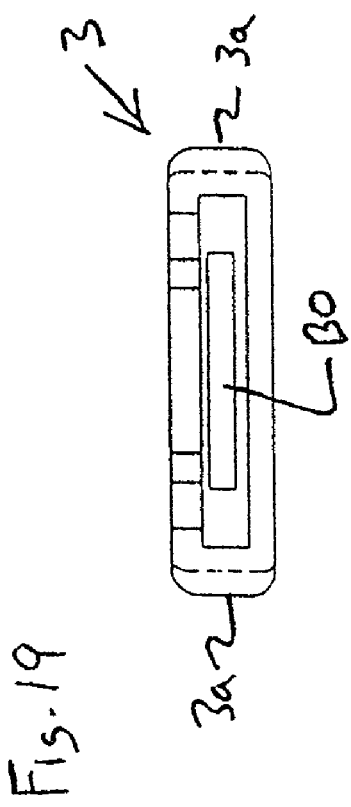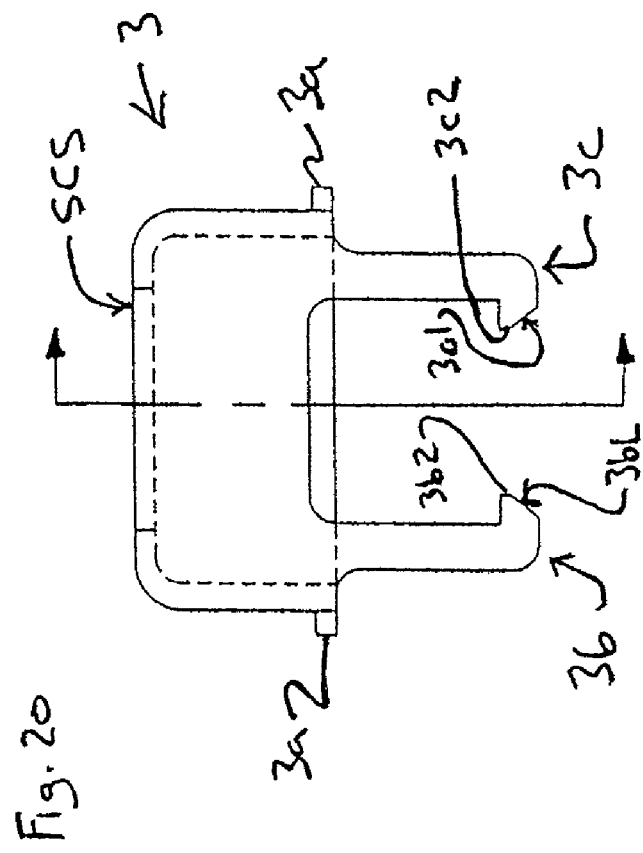

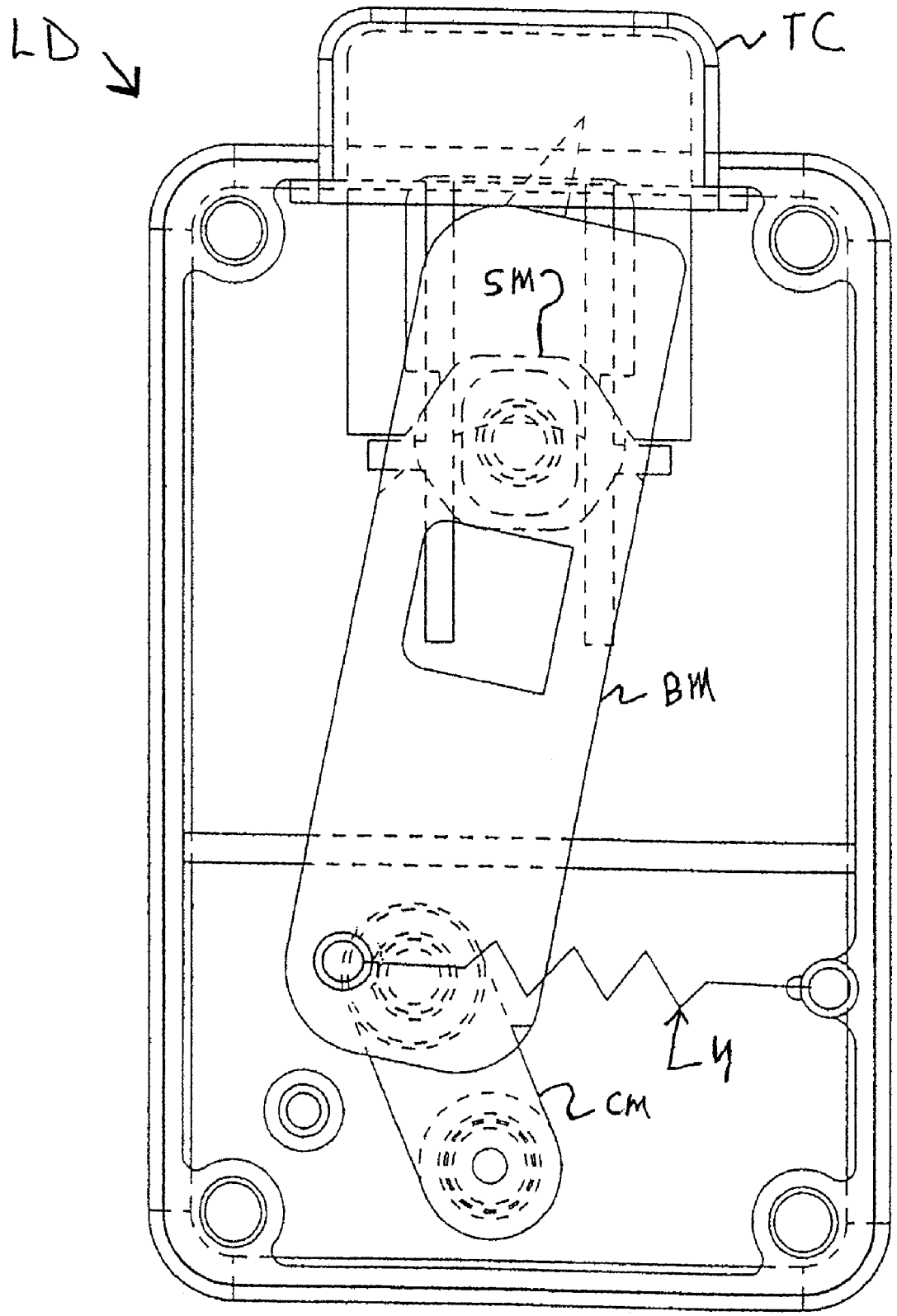

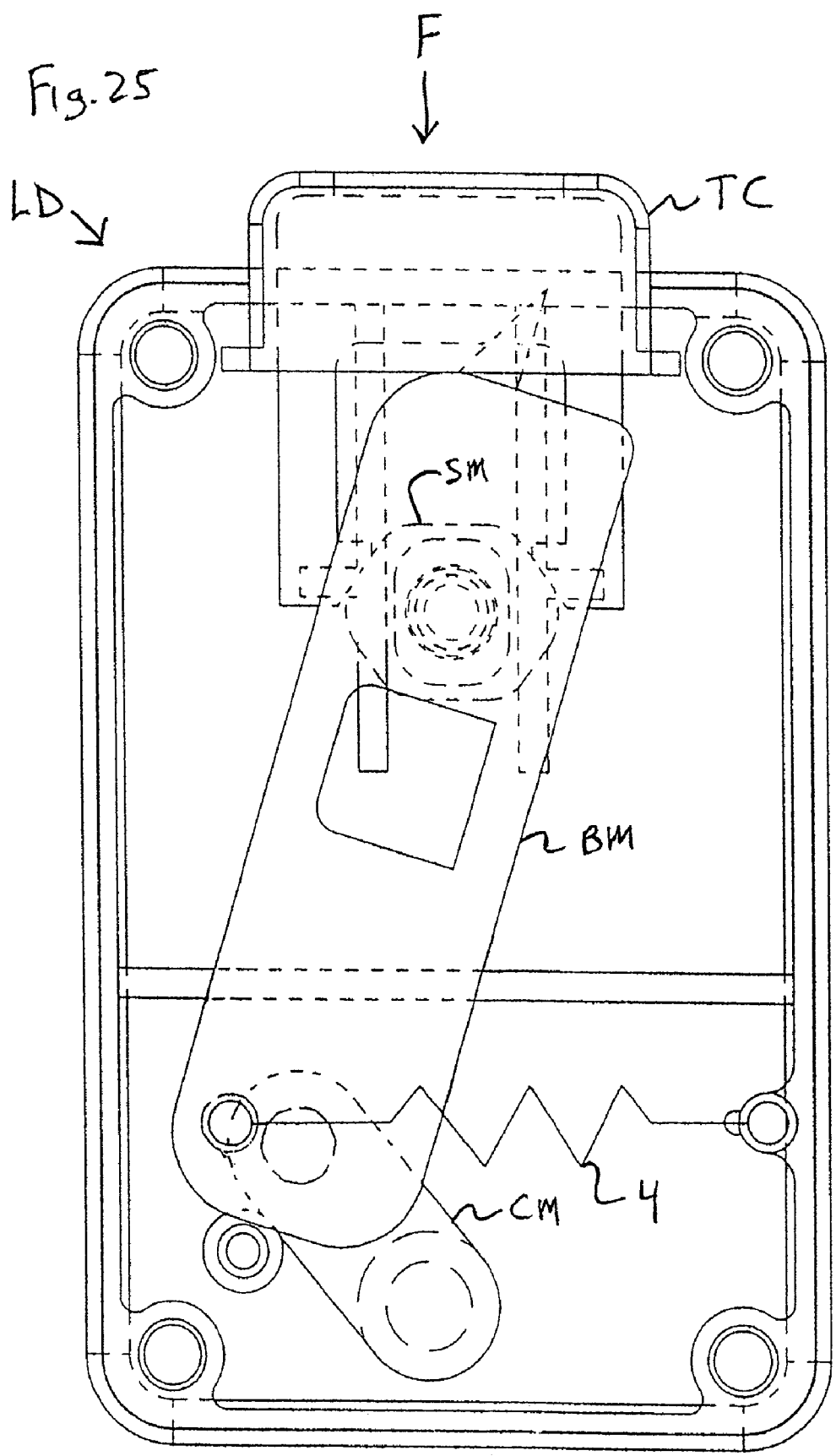

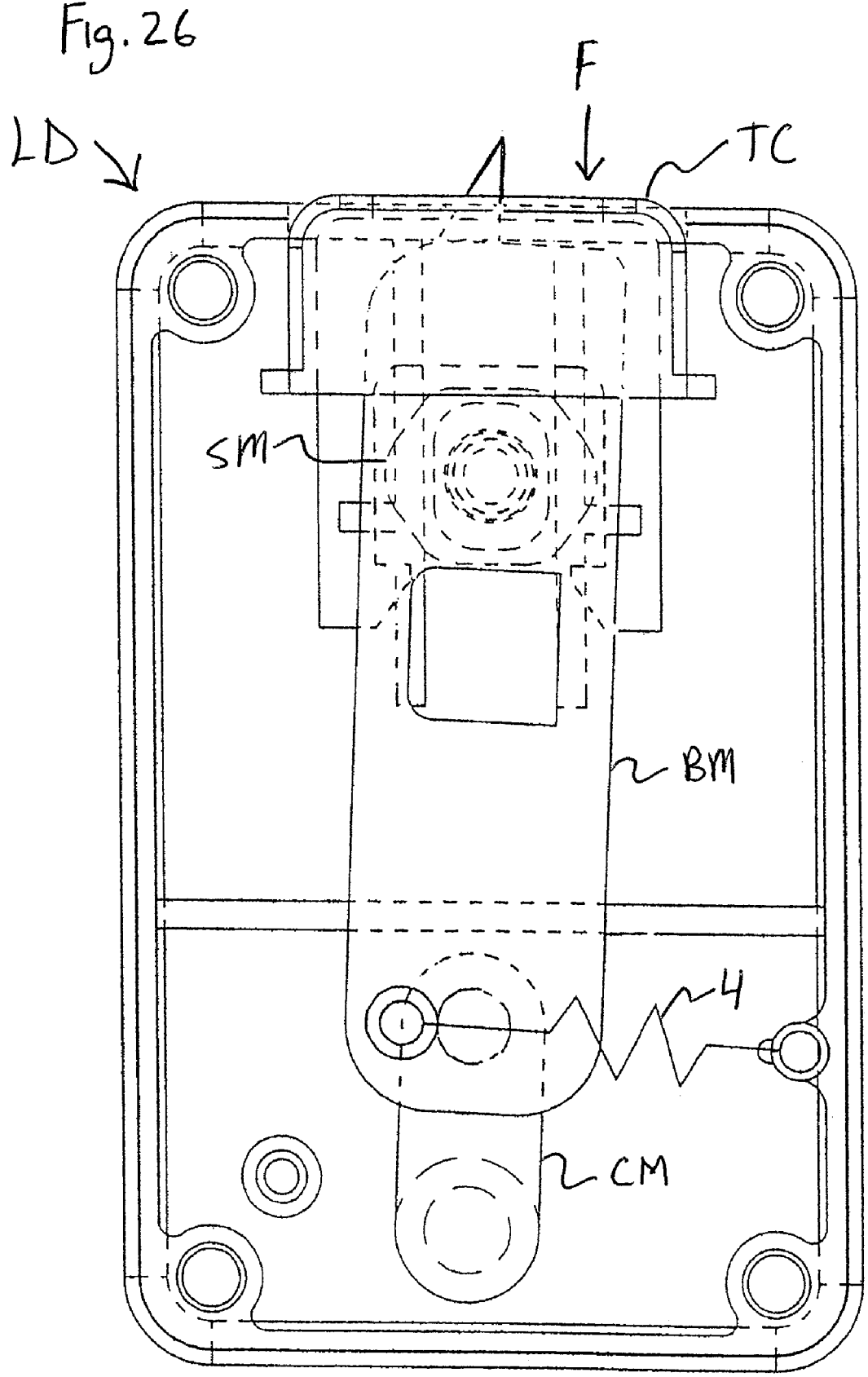

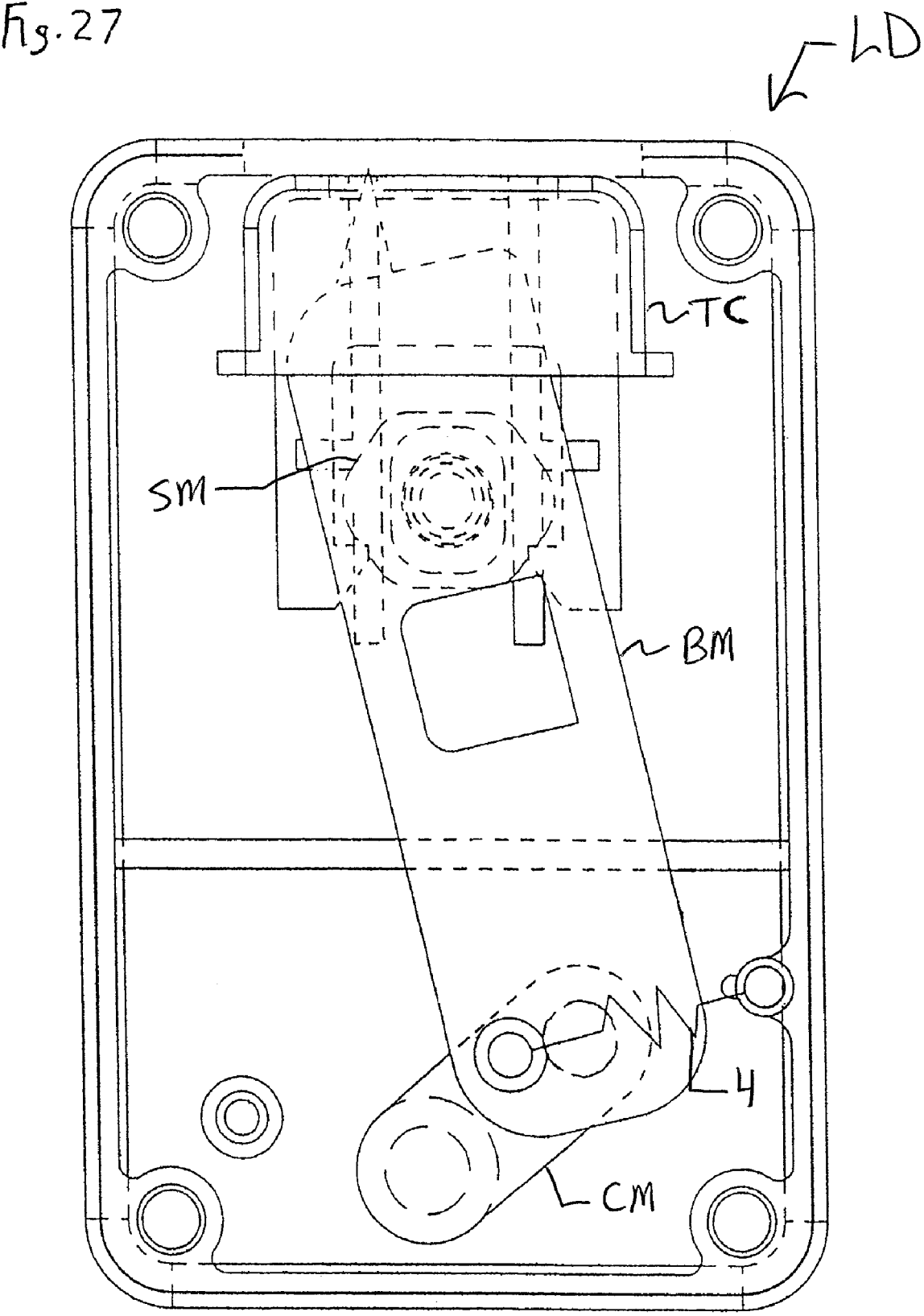

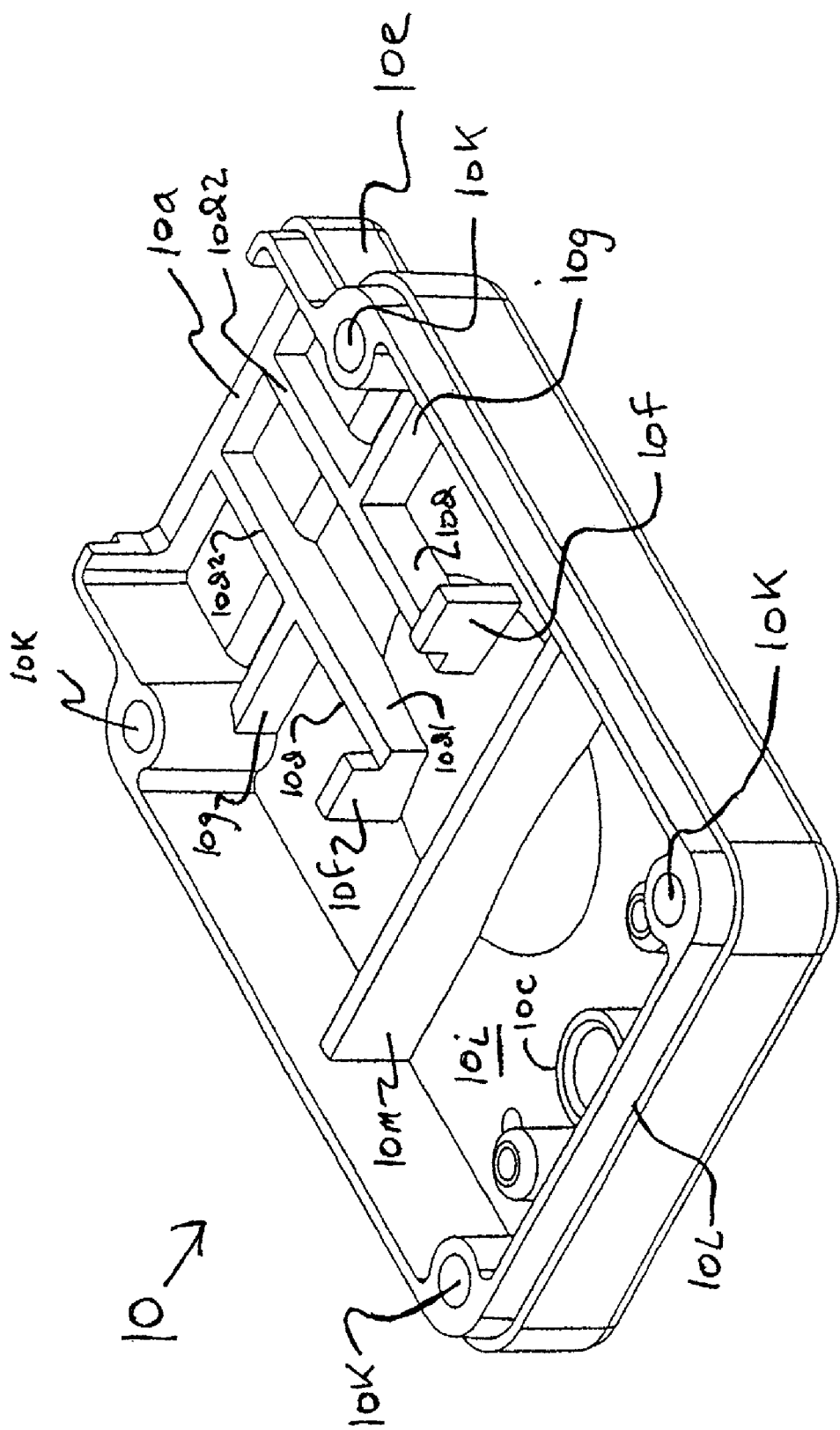

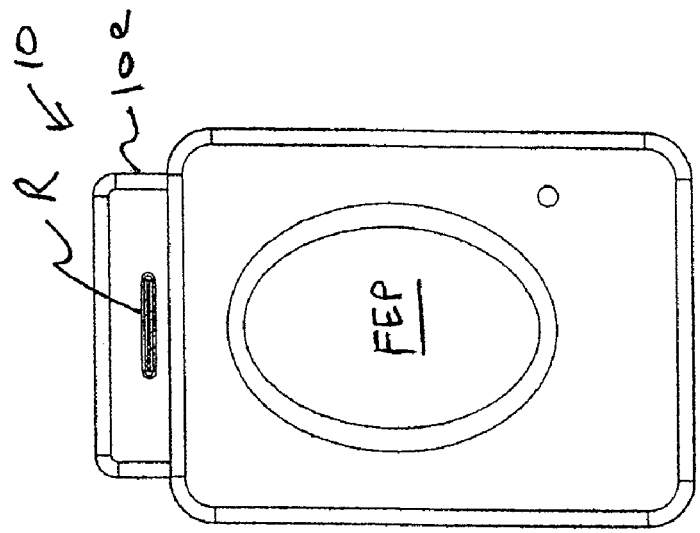
Fig. 35
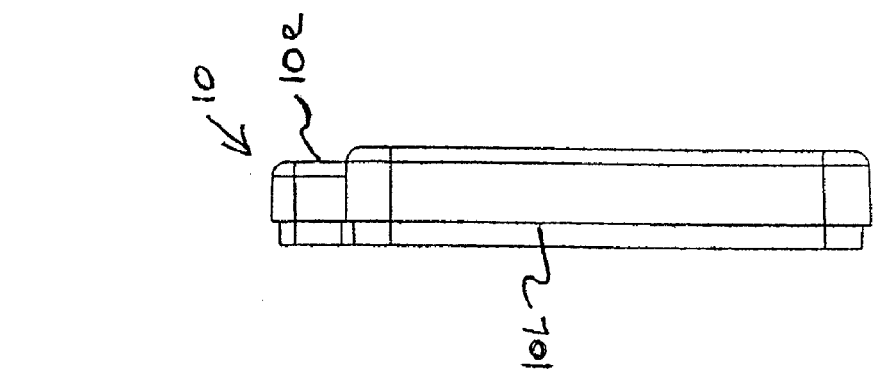
Fig. 34
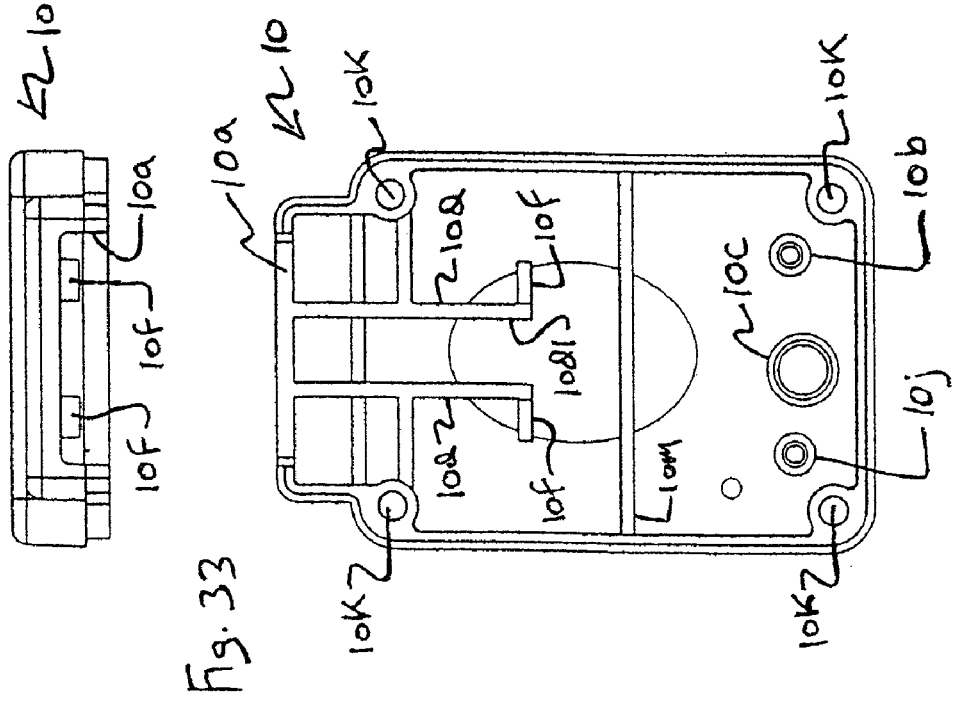
Fig. 32
Fig. 33

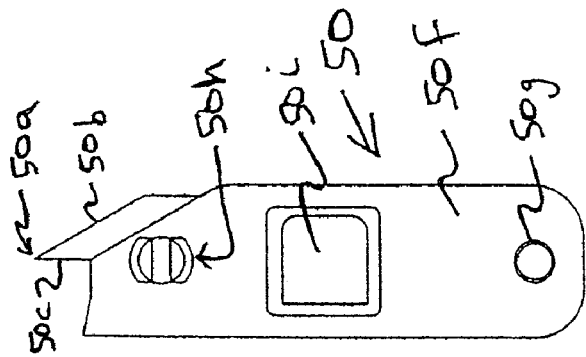
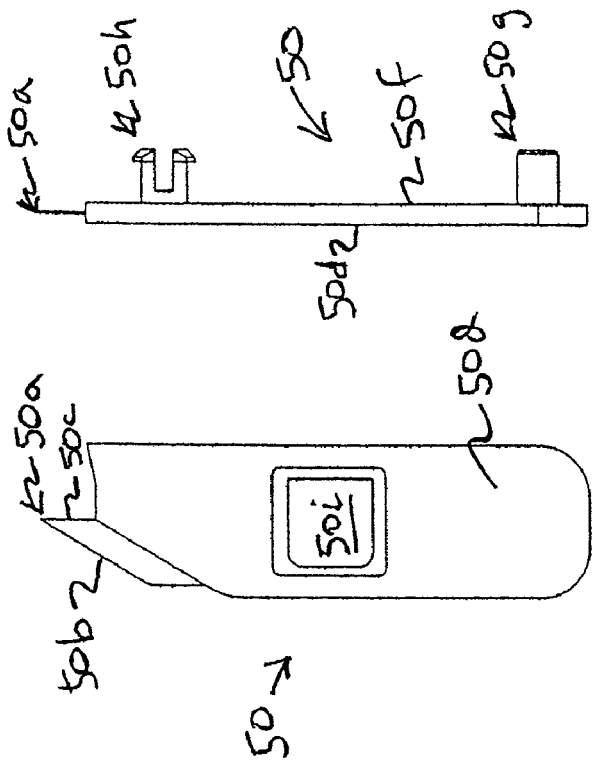
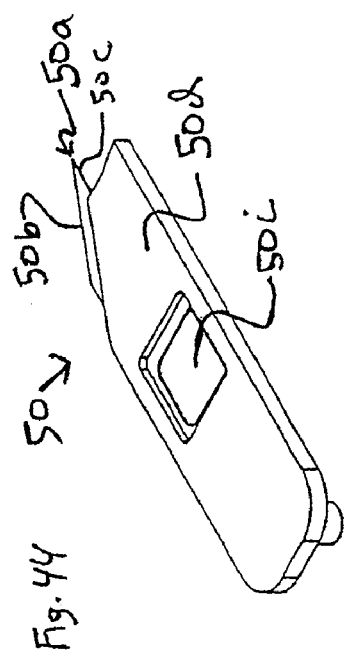

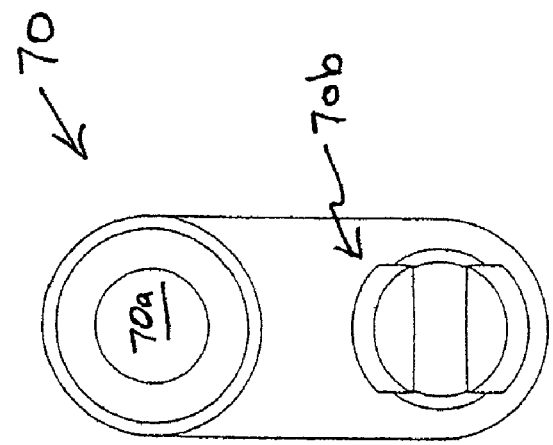
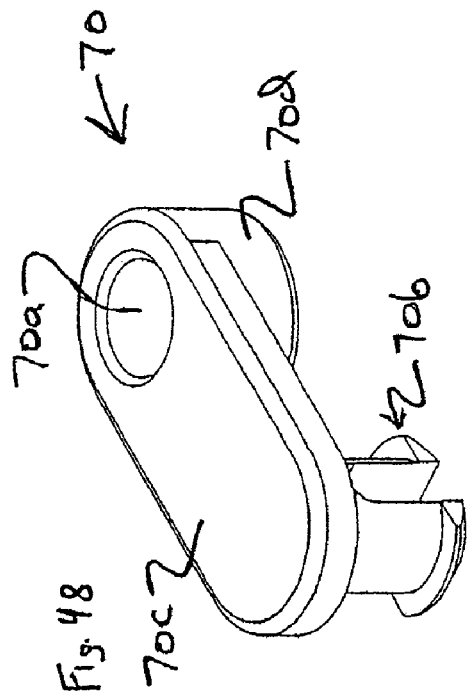
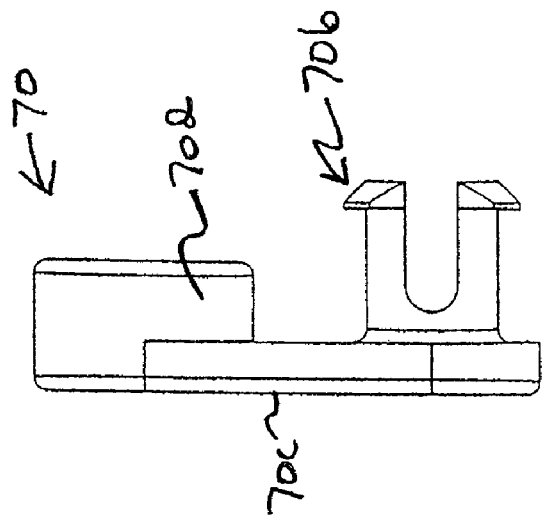
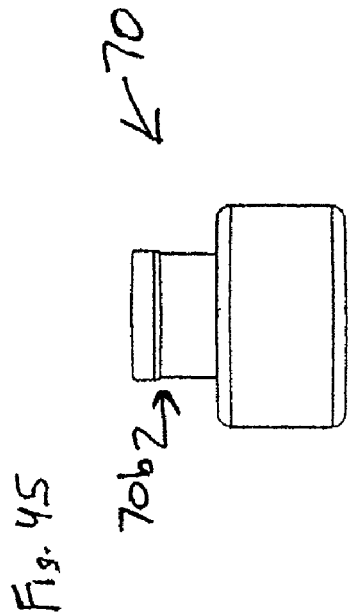
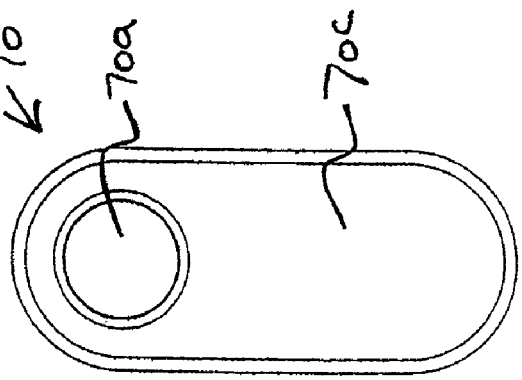

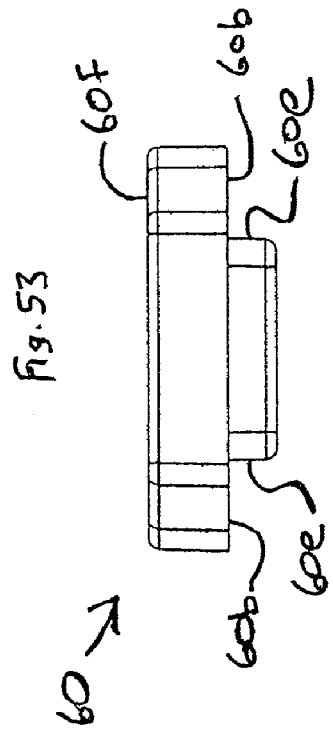
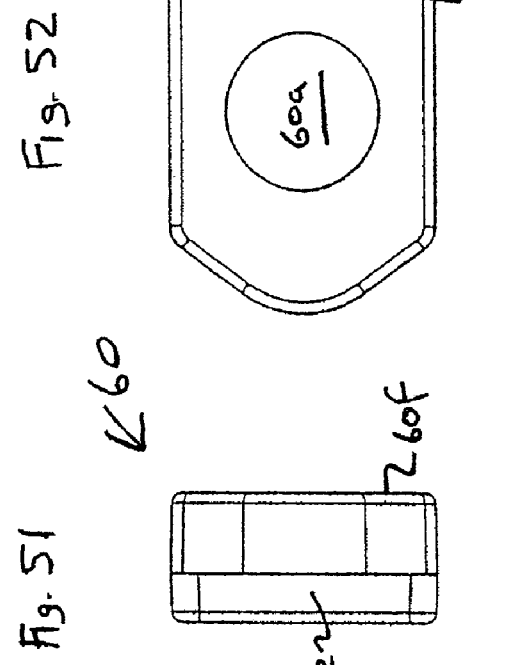
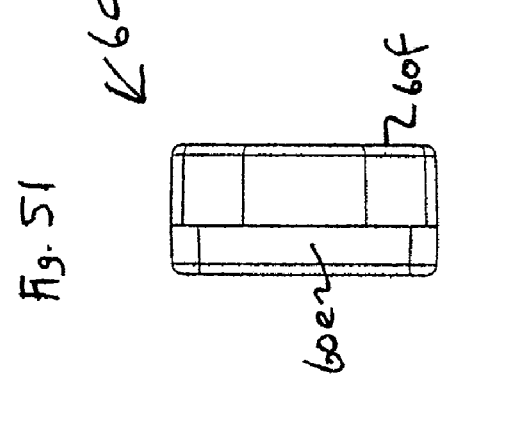
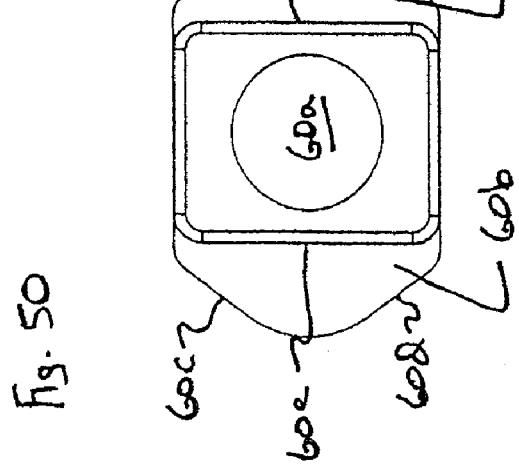

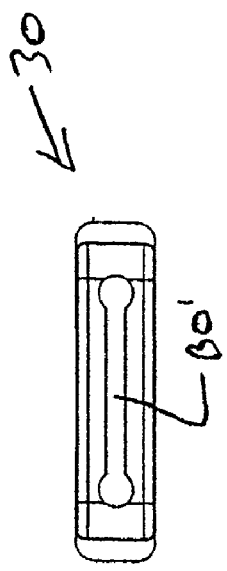
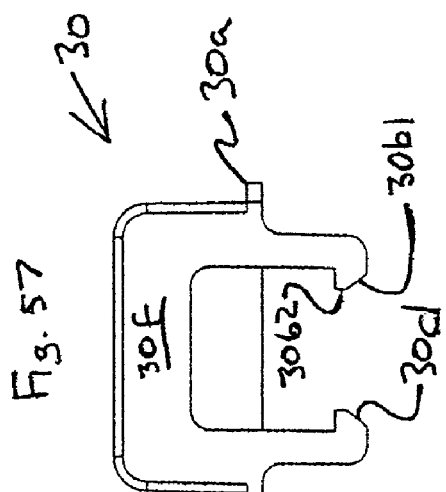
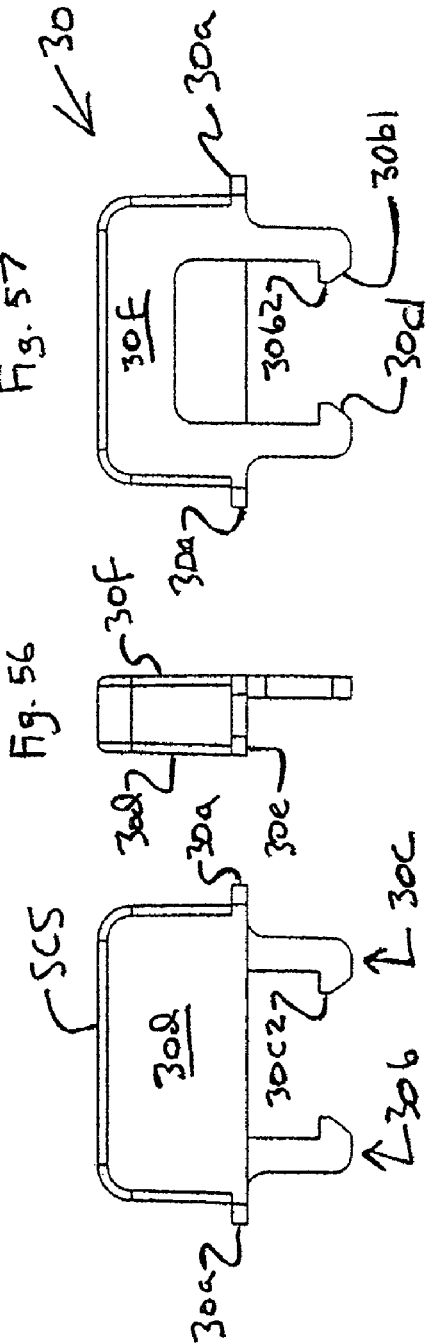
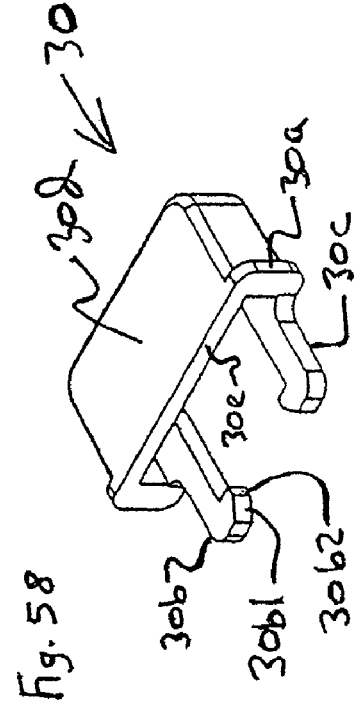

＃ DISPOSABLE/SINGLE-USE BLADE LANCET DEVICE AND METHOD

BACKGROUND OF THE INVENTION

1. Field of the Invention

The invention relates to a disposable and/or single-use blade lancet device, and to a method of using a disposable and/or single-use blade lancet device. In particular, the invention relates to an inexpensive blade lancet device which may be both disposable and/or made for single use, i.e., can be used once and discarded. The blade lancet device has particular application in a medical service environment (e.g., doctor's office, nurse's station, or hospital) in taking a blood sample from an infant by, e.g., pricking the infant's heel, in order to diagnose and/or check for, e.g., bilirubin.

2. Discussion of Background Information

Lancet needle devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Moreover, controlling the depth of penetration cannot be reliably accomplished without the use of a mechanical device. Additionally, many users simply cannot perform the procedure owing to either a fear of needles or because they lack a steady hand. As a result, lancet devices have been developed which allow the user to more easily and reliably perform this procedure.

Incision devices are used to create a small incision in the skin of a user for various purposes such as for determining a bleeding time and for taking a blood sample. However, such devices typically utilize a plunging blade movement which can be painful. Other devices utilize a slicing movement which can also be painful. Still other devices provide for a controlled blade path such that the blade depth increases and decreases between a point of maximum depth. However, such devices are complex and utilize may parts.

An improved device would allow the user to easily, safely, smoothly, and in a less painful manner, form a small incision in the skin. Such a device would also be disposable and inexpensive to use. Finally, such a device would be ergonomically shaped, compact in size, easy to store and package, easy to use, and would overcome some of the disadvantages described above.

Thus, while advances have been made, there is a continuing need for a blade lancet device which provides for convenient, reliable and easy use. The device should also be inexpensively made (i.e., by utilizing fewer parts or components) so that it can be economically used a single time and thereafter disposed of.

SUMMARY OF THE INVENTION

According to one aspect of the invention there is provided a single-use blade lancet device, comprising a body comprising a rear end and a front end. A triggering mechanism comprises a blade tip opening. The triggering mechanism is at least one of associated with the body and mounted to the body. A blade member is movably mounted within the body and comprises a front end and a rear end. The blade member is movable at least between a first retracted position, an extended position, and a second retracted position. A biasing arrangement biases the blade member from the first retracted position towards the extended position and then towards the second retracted position. A guiding arrangement guides the blade member while the blade member moves from the first retracted position towards the extended position and then towards the second retracted position. During movement of the blade member, the guiding arrangement ensures that the blade member both moves along a curved path and slides in a linear direction which is substantially parallel to an axis extending from the blade tip opening to the rear end of the body.

According to one aspect of the invention, the biasing arrangement comprises a spring.

According to one aspect of the invention, the biasing arrangement comprises at least one extension spring.

According to one aspect of the invention, the biasing arrangement comprises at least one torsion spring.

According to one aspect of the invention, the triggering mechanism is movably mounted to the front end of the body.

According to one aspect of the invention, the triggering mechanism comprises a cap portion which, at least in the first retracted position, extends out from the body, and at least one arm arranged within the body.

According to one aspect of the invention, the body comprises a first housing part connected to a second housing part.

According to one aspect of the invention, the blade member comprises a body portion made of one material and a blade tip portion made of a different material.

According to one aspect of the invention, the guiding arrangement comprises two projections coupled to the blade member, a pivotally mounted connecting member, and two substantially parallel guiding members coupled to the body.

According to one aspect of the invention, the guiding arrangement comprises two spaced apart guiding projections coupled to one housing part of the body and two spaced apart guiding projections coupled to another housing part of the body.

According to one aspect of the invention, the guiding arrangement comprises at least two generally circular projections, a movably mounted connecting member, and at least two spaced apart generally linear guide members.

According to one aspect of the invention, the guiding arrangement comprises first and second projections extending from one side of the blade member, a movably mounted connecting member having one end movably connected to the first projection and another end movably connected to a portion of the body, and a slide movably coupled to the second projection and movably guided by two spaced apart members coupled to the body.

According to one aspect of the invention, the guiding arrangement comprises a plurality of non-movable projections, a movably mounted connecting member, guiding members coupled to the body, and a movably guided slide.

According to one aspect of the invention, the triggering mechanism comprises two arms which deflect away from each other to cause automatic movement of the blade member from the first retracted position to the extended position and then to the second retracted position.

According to one aspect of the invention, the front end of the body comprises a generally rectangular-shaped opening which receives therein a generally rectangular-shaped portion of the triggering mechanism.

According to one aspect of the invention, the triggering mechanism comprises at least one arm which deflects to cause automatic movement of the blade member from the first retracted position to another more retracted position, then to the extended position, and then to the second retracted position.

According to one aspect of the invention, the body comprises a generally rectangular-shaped body having ergonomically-shaped finger gripping portions.

According to one aspect of the invention, the device may further comprise a removable cap member which prevents triggering when installed on the body.

According to one aspect of the invention, the body is a generally rectangular-shaped body which comprises two generally planar sides defining a thickness, wherein each said side has a finger gripping portion, and wherein the thickness is less than half of a width of the body and less than half of the length of the body, whereby the length is measured between the front and rear ends of the body.

According to one aspect of the invention, the width is less than the length of the body.

According to one aspect of the invention, the device may further comprise a removable safety device configured to prevent movement of the blade member.

According to one aspect of the invention, the blade member comprises generally rectangular-shaped metal plate with a pointed blade tip defined by a tapered sharpened edge and a straight blunt edge.

According to one aspect of the invention, the guiding arrangement guides a blade tip of the blade member along a curved path.

According to one aspect of the invention, the guiding arrangement guides a blade tip of the blade member along a partially circular path.

According to one aspect of the invention, the body comprises oppositely arranged projecting ribs which movably guide the blade member.

According to one aspect of the invention, the blade member is pivotally mounted at two spaced apart locations.

According to one aspect of the invention, the blade member comprises a width, a thickness and a length, wherein the width is less than the length, and wherein the width is greater than the thickness by a factor of at least five.

According to one aspect of the invention, the blade member comprises a width, a thickness and a length, wherein the width is less than the length, and wherein the width is greater than the thickness by a factor of at least ten.

According to one aspect of the invention, the guiding arrangement at least comprises two spaced apart ribs coupled to the body, a slide linearly guided by the two spaced apart ribs, a fist projection of the blade member extending into an opening of the slide, and a connecting member having one end movably mounted to a projection of the body and another end movably connected to a second projection of the blade member.

According to one aspect of the invention, the body comprises at least one opening through which a portion of the triggering mechanism protrudes.

According to one aspect of the invention, the body comprises an ergonomic shape to facilitate gripping.

According to one aspect of the invention, the body comprises a two-piece plastic body and the triggering mechanism comprises a one-piece member having a cap portion and two deflecting arms.

According to one aspect of the invention, the body comprises a two-piece plastic body.

According to one aspect of the invention, the body comprises internal projecting fins which guide the movement of the blade member within the body.

According to one aspect of the invention, the blade tip opening is a rectangular-shaped opening.

According to one aspect of the invention, the blade tip opening is a rectangular-shaped slot.

According to one aspect of the invention, there is provided a method of puncturing a surface of skin using any of the devices described herein, wherein the method comprises disposing a front end of the device against a user's skin, forcing the device against the user's skin in order to activate the triggering mechanism and thereby cause a blade tip of the blade member to penetrate and cut the user's skin, and preventing the user from moving the blade member to the extended position and to the first retracted position.

According to one aspect of the invention, there is provided a method of puncturing a surface of skin using any of the devices described herein, wherein the method comprises disposing the device against a user's skin, moving the triggering mechanism to automatically cause a blade tip of the blade member to penetrate the user's skin, and preventing the user from moving the blade member to the extended position and to the first retracted position.

According to one aspect of the invention, there is provided a method of puncturing a surface of skin using any of the devices described herein, wherein the method comprises disposing a front end of the device against a user's skin, causing the triggering mechanism to move into the body thereby causing movement of the blade member from the first retracted position to another more retracted position, then to the extended position and then to the second retracted position, and preventing the triggering mechanism from moving back to an initial position prior to the causing.

According to one aspect of the invention, there is provided a method of puncturing a surface of skin using any of the devices described herein, wherein the method comprises disposing a front end of the device against a user's skin, triggering the triggering mechanism to cause a blade tip of the blade member to penetrate the user's skin, and preventing the user from moving the triggering mechanism to an original armed or extended position.

According to one aspect of the invention, there is provided a method of puncturing a surface of skin using any of the devices described herein, wherein the method comprises removing a removable safety device or cap from the body, disposing the triggering mechanism against a user's skin, and triggering the device to cause movement of the blade member.

According to one aspect of the invention, there is provided a method of puncturing a surface of skin using any of the devices described herein, wherein the method comprises removing a removable safety device or cap from the body, disposing the device against a user's skin, and triggering the device to cause movement of the blade member.

According to one aspect of the invention, there is provided a method of puncturing a surface of skin using any of the devices described herein, wherein the method comprises removing a removable safety device from engagement with the front end of the body, disposing a front end of the device against a user's skin, and moving the triggering mechanism into the body to cause movement of the blade member.

According to one aspect of the invention, there is provided a method of puncturing a surface of skin using any of the devices described herein, wherein the method comprises removing a removable safety device from engagement with the device, disposing a front end of the device against a user's skin, and triggering the triggering mechanism to cause movement of the blade member.

According to one aspect of the invention, there is provided a disposable and single-use blade lancet device, comprising a body comprising a rear end and a front end, a cap member arranged at the front end of the body and comprising a blade tip opening, a blade member movably mounted within the body and comprising a front end and a rear end, the blade member being movable at least between a first retracted position, an extended position, and a second retracted position that is different than the first retracted position, a biasing device that causes movement of the blade member from the first retracted position towards the extended position and then towards the second retracted position, and a guiding arrangement that at least comprises first and second projections, a connecting member movably coupled to the first projection and a portion of the body, and a slide movably coupled to the second projection and slidably engagable with another portion of the body, wherein the guiding arrangement guides the blade member while the blade member moves from the first retracted position towards the extended position and then towards the second retracted position.

According to one aspect of the invention, the cap member comprises a triggering mechanism, whereby movement of the cap member to a predetermined location automatically causes movement of the blade member from the first retracted position towards the extended position and then towards the second retracted position.

According to one aspect of the invention, the body comprises a generally rectangular-shaped body.

According to one aspect of the invention, the guiding arrangement guides the rear end of the blade member along a first curved path while the front end of the blade member moves linearly and along a second curved path that is shorter than the first curved path.

According to one aspect of the invention, the first and second projections are connected to the blade member.

According to one aspect of the invention, the first and second projections are integrally formed with the blade member.

According to one aspect of the invention, there is provided a disposable and single-use blade lancet device, comprising a body comprising a rear end and a front end, a trigger device having a blade tip opening and being at least one of associated with the body and mounted to the body, a blade member movably mounted within the body and comprising a front portion and a rear portion, the blade member being movable between a first retracted position, an extended position, and a second retracted position, a biasing arrangement that biases the blade member from the first retracted position towards the extended position and then towards the second retracted position, and a guiding arrangement guides the blade member while the blade member moves from the first retracted position towards the extended position and then towards the second retracted position, wherein the guiding arrangement comprises a slide which linearly guides the front portion of the blade member and a connecting member which guides the rear portion of the blade member along a curved path.

According to one aspect of the invention, the guiding arrangement further comprises first and second spaced apart projections extending from one side of the blade member, the first projection being movably mounted to the connecting member and the second projection being movably mounted to the slide.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein:

FIG. 14 shows a side view of the blade member of FIG. 11;

FIG. 19 shows an inside view of the trigger cap used in the embodiment of FIG. 1;

FIG. 20 shows a rear view of the trigger cap shown in FIG. 19;

FIG. 21 shows a cross-section of the trigger cap shown in FIG. 20;

FIG. 24 shows another embodiment of the blade lancet device in a fully assembled state. The protective cap is not shown. The body is transparent and has a front end configuration that is different from that of FIG. 1, otherwise the remaining parts are similar to those of FIG. 1. This embodiment illustrates the positions of the blade member, the connecting member, the spring, the slide member, and the trigger cap when the blade member is in the first retracted position for the embodiments shown in FIGS. 1 and 28, as well as for the embodiment shown in FIG. 24;

FIG. 25 shows the embodiment of FIG. 24 after the trigger cap has moved into the body slightly thereby causing the connecting member to contact a stop projection in the lower housing part. This movement causes additional retraction of the blade member and additional extension of the spring. The movement of the trigger cap occurs when a user forces the trigger cap against a portion of one's body;

FIG. 26 shows the embodiment of FIG. 24 after the trigger cap has moved fully into the body thereby causing the deflecting arms to engage with and then pass by the slide member. This movement causes the blade member to move to the extended position under the action of the spring. The movement of the trigger cap occurs when a user further forces the trigger cap against a portion of one's body;

FIG. 27 shows the embodiment of FIG. 24 after the blade member has moved to the second retracted position under the action of the spring. In this position, the trigger cap is prevented from moving back to the position shown in FIG. 24 by engagement between the slide member and the deflecting arms of the trigger cap. Moreover, due to the biasing force of the spring, the blade member is prevented from moving back to the extended position and is thereby safely held in the body;

FIG. 31 shows an inside perspective view of the lower housing part of the embodiment shown in FIG. 28;

FIG. 32 shows a top view of FIG. 31;

FIG. 33 shows an inside view of the lower housing part of FIG. 31;

FIG. 34 shows a side view of the lower housing part of FIG. 31;

FIG. 35 shows a rear side view of FIG. 31;

FIG. 41 shows a front view of the blade member used in the embodiment of FIG. 28;

FIG. 42 shows a side view of the blade member of FIG. 41;

FIG. 43 shows a rear view of FIG. 41;

FIG. 44 shows a front perspective view of the blade member of FIG. 41;

FIG. 45 shows an end view of the connecting member used in the embodiment shown in FIG. 28;

FIG. 46 shows a front view of the connecting member of FIG. 45;

FIG. 47 shows a side view of the connecting member shown in FIG. 45;

FIG. 48 shows a front perspective view of the connecting member shown in FIG. 45;

FIG. 49 shows a rear view of the connecting member shown in FIG. 45;

FIG. 50 shows a rear view of the slide member used in the embodiment shown in FIG. 28;

FIG. 51 shows a side view of the slide member shown in FIG. 50;

FIG. 52 shows a front view of the slide member shown in FIG. 50;

FIG. 53 shows a top end view of the slide member shown in FIG. 50;

FIG. 54 shows a top view of the trigger cap used in the embodiment shown in FIG. 28;

FIG. 55 shows a front view of the trigger cap shown in FIG. 54;

FIG. 56 shows a side view of the trigger cap shown in FIG. 54;

FIG. 57 shows a rear view of the trigger cap shown in FIG. 54;

FIG. 58 shows a front perspective view of the trigger cap shown in FIG. 54;

DETAILED DESCRIPTION OF THE PRESENT INVENTION

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

Figure 13:
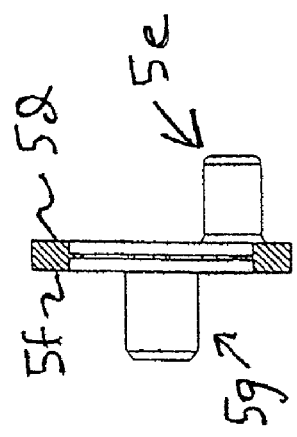
FIG. 13 shows a cross-section view of FIG. 12.
Figure 11:
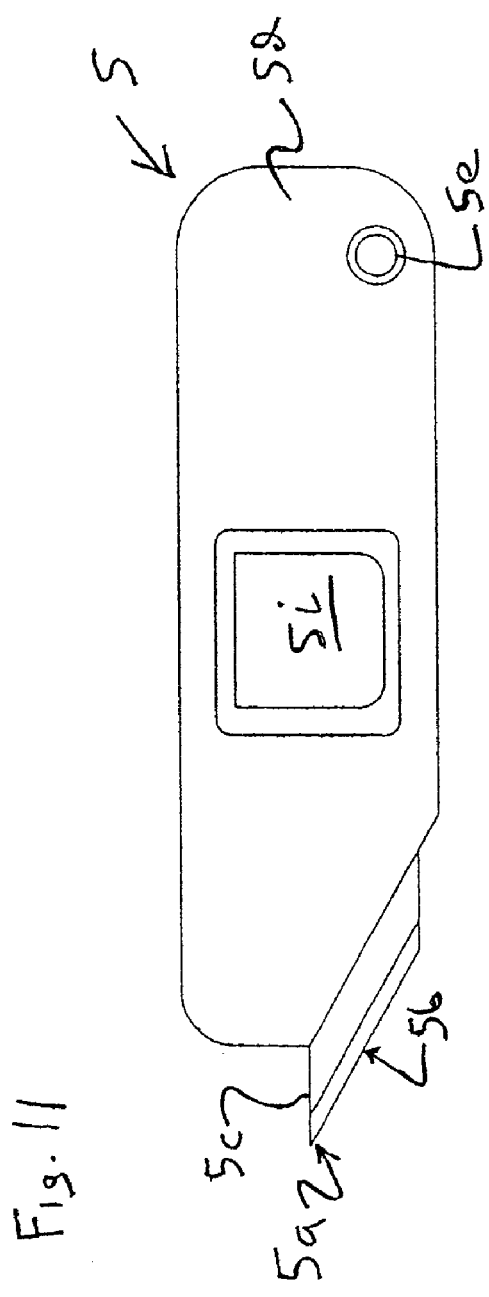
FIG. 11 shows a front view of the blade member used in the embodiment of FIG. 1.
Figure 12:
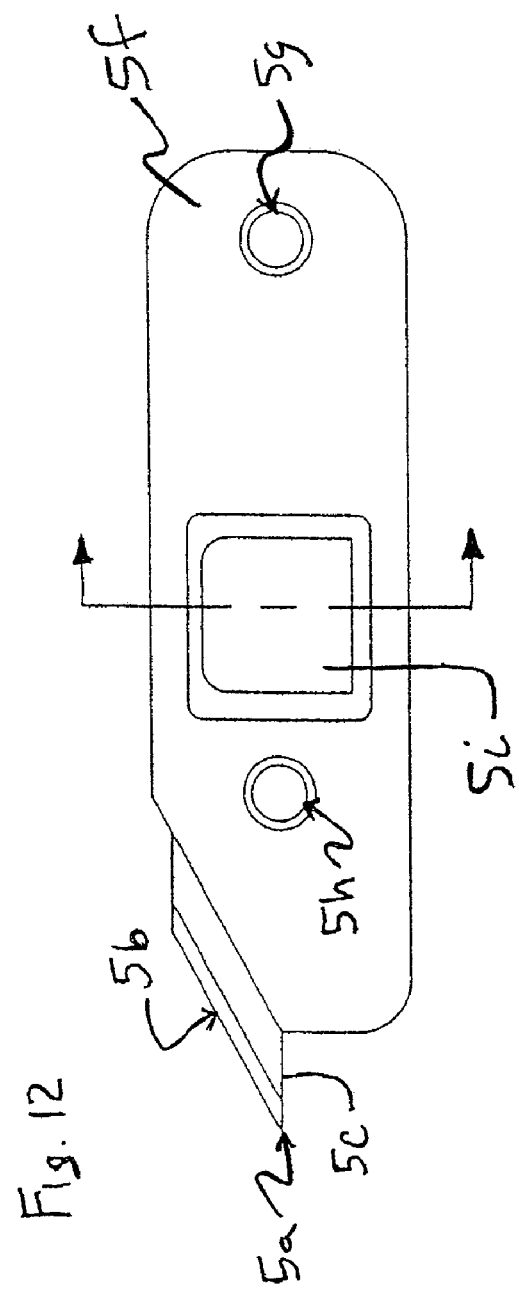
FIG. 12 shows a rear view of the blade member shown in FIG. 11.

FIGS. 1-23 show a first non-limiting embodiment of a single-use and/or disposable blade lancet device LD. Lancet device LD has a lancet body made up of an upper or front body portion 2 and a lower or rear body portion 1. These parts 1 and 2 are connected to each other, e.g., using adhesives and/or fasteners and/or welding and/or snap-together holding mechanisms (not shown), when the lancet device LD is initially assembled. Preferably, the housing members 1 and 2 are connected together using projections and openings, as shown in the drawings. A blade member 5 (see FIGS. 11-13) is movably disposed within the body parts 1, 2 (e.g., in a manner similar to that shown in the embodiment of FIGS. 24-27). A front end cover or protective cap PC (see also FIGS. 22-23) is removably connected or attached to a front portion 1e/2e of the body parts 1, 2. The protective cap PC can also be similar to the one exemplified in copending U.S. patent application Ser. No. 10/441,065 filed on May 20, 2003, the entire disclosure of which is hereby expressly incorporated by reference in its entirety.

As with many lancet devices, the lancet device defines a plane or surface SCS which is, e.g., configured to contact (i.e., be positioned against) a user's skin. However, the instant embodiment may also utilize either an outwardly curved or an outwardly curved skin engaging surface SCS beyond which the tip portion 5a of the lancet blade member 5 (see FIGS. 11-13) can extend and/or project. Of course, the invention also contemplates using a planar front skin engaging surface SCS shown herein and also of the type described in, e.g., U.S. Pat. No. 6,258,112, the disclosure of which is hereby expressly incorporated by reference in its entirety.

Figure 1:
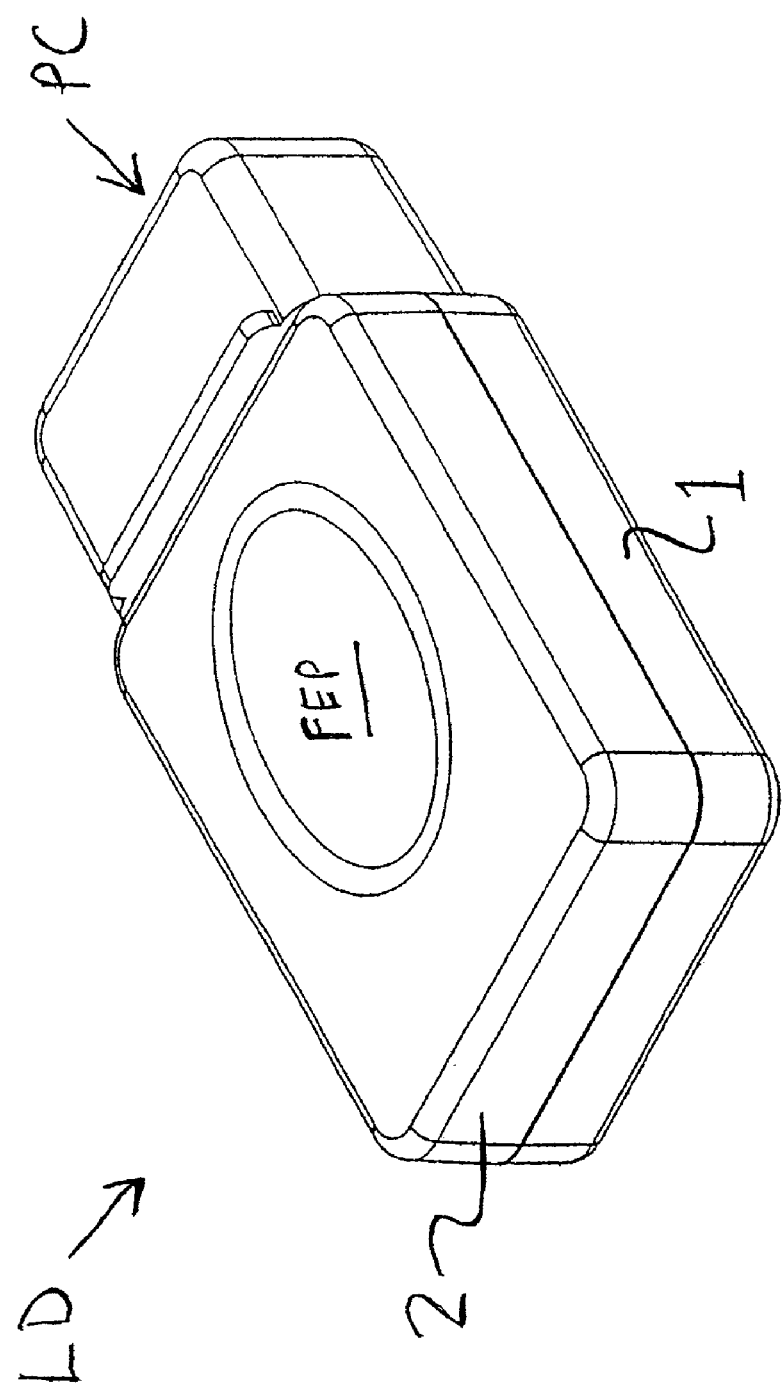
FIG. 1 shows a front view of one embodiment of the disposable and single-use blade lancet device with the protective cap installed thereon.
Figure 3:
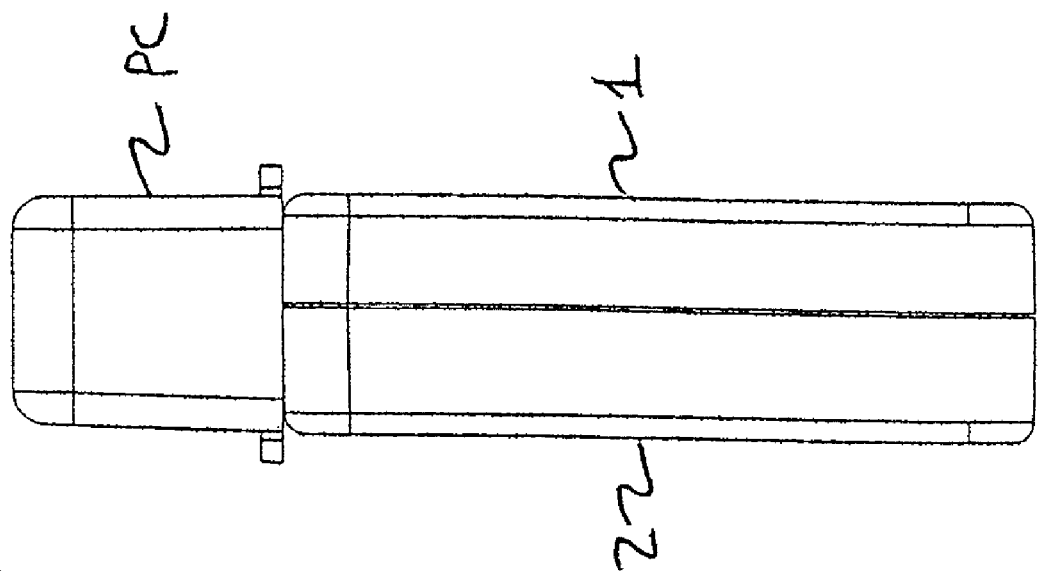
FIG. 3 shows a side view of the embodiment shown in FIG. 1.
Figure 2:
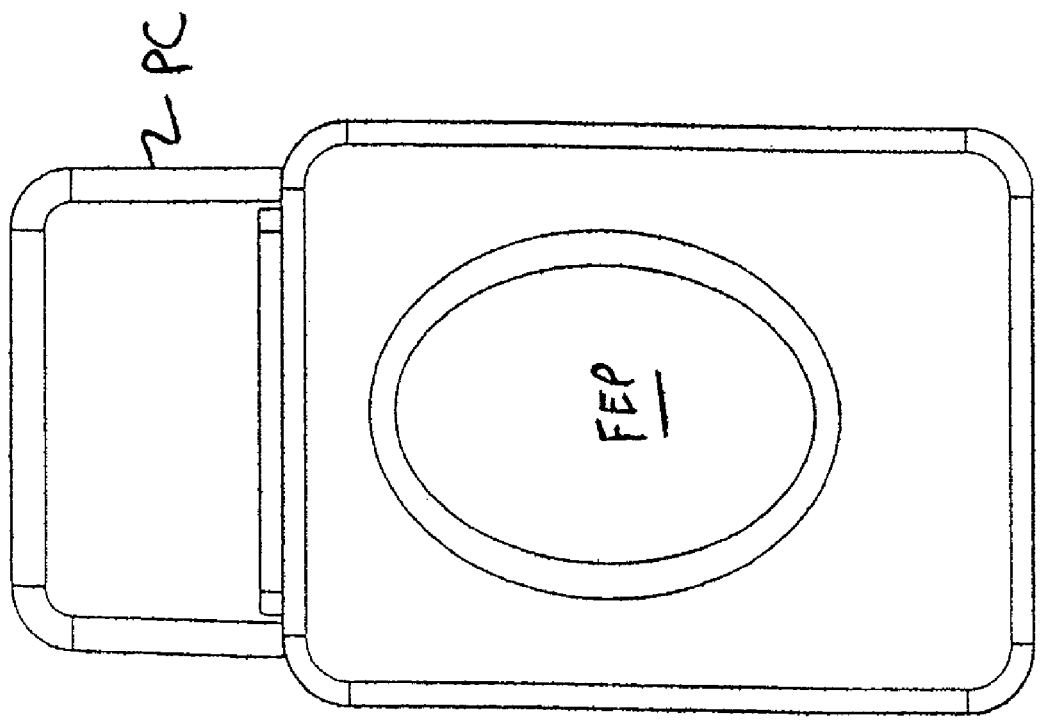
FIG. 2 shows a front view of the embodiment of FIG. 1.

As can be seen in FIGS. 1-3, the lancet body 2/1 can have a generally rectangular shape and can preferably also have an ergonomic shape to facilitate comfortable gripping/holding.

Of course, the invention contemplates other shapes for the lancet body provided that they result in a relatively inexpensive design and/or which is economical to produce. As explained above, the front end of the lancet device LD includes a skin engaging surface SCS which is defined by outer surface of the trigger cap 3 (see FIGS. 19-21). A lancet blade opening BO extends through an end wall of the trigger cap 3 and serves to allow the tip of lancet blade member 5 to penetrate beyond the surface SCS (see e.g., FIG. 26). In this regard, the trigger cap 3 is movably mounted to the front end portion of the lancet body. In the instant embodiment, the trigger cap 3 is a generally rectangular-shaped cap member for reasons of aesthetic design. However, the invention contemplates a variety of shapes for the trigger cap 3 such as, e.g., oval, triangular, square, polygonal, etc,. Moreover, in the instant embodiment, the trigger cap 3 is generally centrally mounted, relative to the sides of the lancet body. However, the invention contemplates other locations and/or positions for the trigger cap 3, provided such locations allow the lancet device to function properly. Other ways of associating the trigger cap 3 on the lancet body are expressly contemplated, such as, e.g., being integral with the housing and acting as a living hinge or spring. The trigger cap 3 is installed in an opening formed by partial openings 1a and 2a of the front cover 2 and rear cover 1 and is sized to slide within the opening in a smooth low-friction manner. As can be seen in FIGS. 19-21, the trigger cap 3 has shoulders 3a which engage inner surfaces of the opening 1a/2a (see e.g., FIG. 24) whereby the trigger cap 3 is prevented from falling out of the lancet body once installed. The trigger cap 3 is also sized to be slid into and/or be pushed into the lancet body (see e.g., FIGS. 25 and 26). However, this movement is resisted owing to the fact that the trigger cap 3 is biased towards an extended position (see e.g., FIG. 24) via a coil extension spring 4 and also by virtue of engagement between the slide member 6 and the deflecting arms 3b and 3c. This biasing force and engagement can be overcome, however, when the trigger cap 3 is pushed into the lancet body sufficiently (see e.g., FIGS. 25 and 26) by applying a force to the surface SCS. Furthermore, because the trigger cap 3 includes an opening BO, once triggered, the blade tip 5a will be allowed to pass therethrough (see e.g., FIG. 26) in order to penetrate a user's skin. Moreover, because the trigger cap 3 also includes the deflecting arms 3b and 3c and, due to the tapered surfaces 6c and 6d, the trigger cap 3 is prevented from moving back to a pre-triggered position by the slide member 6, the blade member 5, the connecting member 7, and the spring 4. Thus, once triggered, the lancet device LD is automatically rendered unusable again—thereby rendering the device a single-use device, a safe device because the blade member 5 is safely contained in the housing, and a device which can be disposed of safely.

Although not shown, the lancet body can preferably includes a viewing opening. Alternatively, it can be made of a transparent/translucent material (see embodiment shown in FIGS. 24-27) so that the user can view the inner workings of the device and will be able to easily note that the device is properly set and/or has not be used. If a viewing opening or window is instead utilizes, it can be formed in the front cover 2 and can be arranged in a convenient area which allows the user to see the position of the blade member 5. The opening or window, of course, can have any desired shape or configuration and can be located at any desired location provided that the user is able to discern the setting position of the blade member 5. If a viewing window is utilized, it can preferable be in the area of the finger engaging/gripping portions or indentations FEP.

In the embodiment shown in FIGS. 1-23, the lancet device is designed to be procured and/or purchased in a pre-loaded arrangement (see FIGS. 1-3). In order to used the lancet device a single time, a user need only remove the protective cap PC (which can be discarded) and, while gripping oppositely arranged portions FEP, and press the trigger cap 3 against the skin of a patient to use it. Once triggered, however, the user will be unable to use the device again owing to the fact that this embodiment contains no mechanism for forcing or moving the blade member 5 from the position shown in, e.g., FIG. 27 to the armed or retracted position shown in, e.g., FIG. 24. Moreover, because, before triggering, the spring 4 maintains the blade member 5 in the position shown in, e.g., FIG. 24, the lancet blade member 5, and particularly the tip portion 5a, is kept safely within the lancet body. Furthermore, because, after triggering, the spring 4 maintains the blade member 5 in the position shown in, e.g., FIG. 27, the lancet blade member 5, and particularly the tip portion 5a, is also kept safely within the lancet body. Additionally, because of, after triggering, the engagement between the slide member 6 (and in particular surfaces 6c) and the arms 3b and 3c (and in particular surfaces 3b1 and 3c1) of the trigger cap 3, the user will be unable to move the trigger cap 3 back to the position shown in FIG. 24 and thereby prevent use the device again.

By way of non-limiting example, the armed position of the blade member 5, trigger cap 3, connecting member 7, slide member 6, and spring 4 shown in, e.g., FIG. 24, can be set when the lancet device is manufactured and/or assembled, i.e., in a factory setting.

With reference to FIGS. 4-7, it can be seen that the rear body or lower housing part 1 can preferably be made as one-piece structure by e.g., injection molding. In this regard, it is preferably made of a plastic or synthetic resin such as, e.g., ABS plastic. The lower body part 1 may also be made of ABS—Metallic Silver and have a finish designated as SPI-A2. Of course, other materials and/or finishes may be utilized, without leaving the scope of the invention. Additionally, the lower body part 1 may have an overall length (measured vertically across FIG. 4) that is approximately 40 mm and an overall width (measured horizontally across FIG. 4) of approximately 26 mm. Although undesirable for reasons of cost, the lower body part 1 may even be made of a plurality of sections of parts which are joined together to form the complete lower body part 1, without leaving the scope of the invention.

Figure 4:
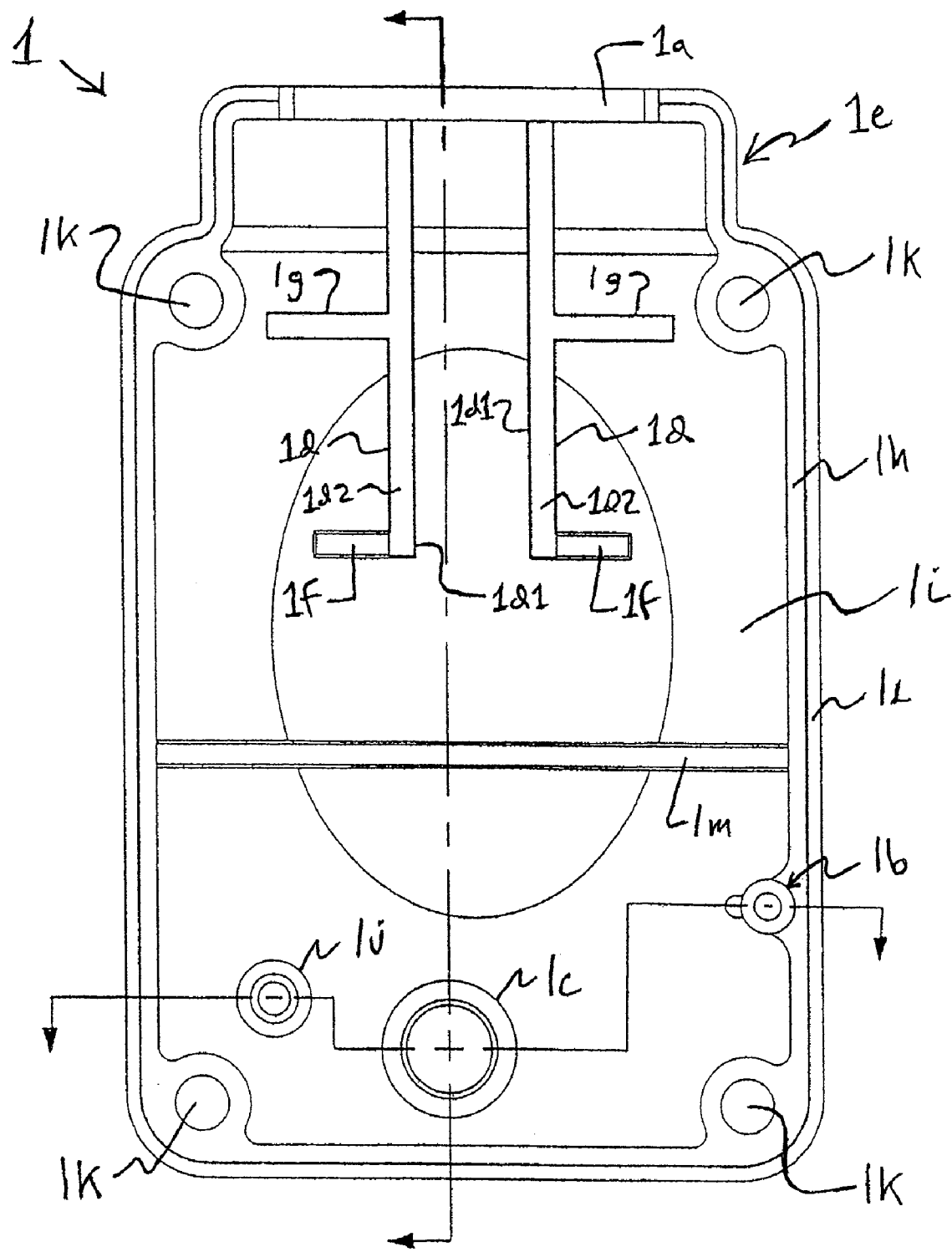
FIG. 4 shows an inside view of the lower housing part of the embodiment shown in FIG. 1.
Figure 5:
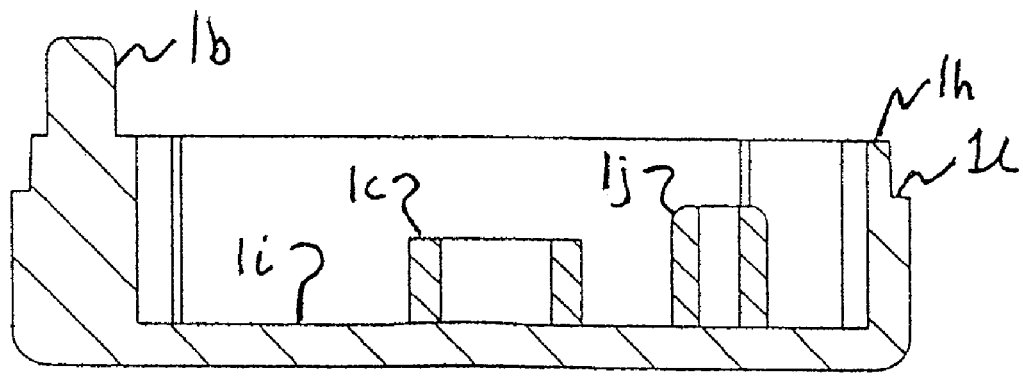
FIG. 5 shows a top cross-section view of FIG. 4.
Figure 6:
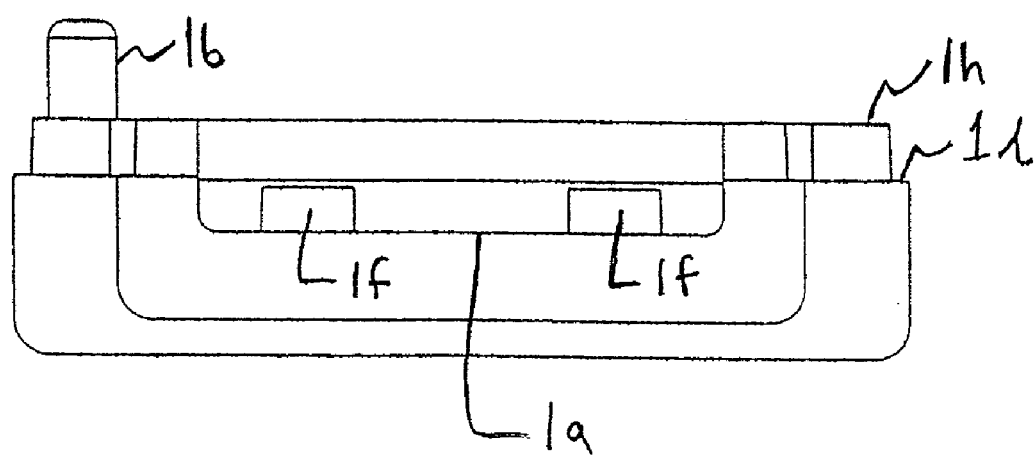
FIG. 6 shows a top view of the lower housing part of FIG. 4.
Figure 7:
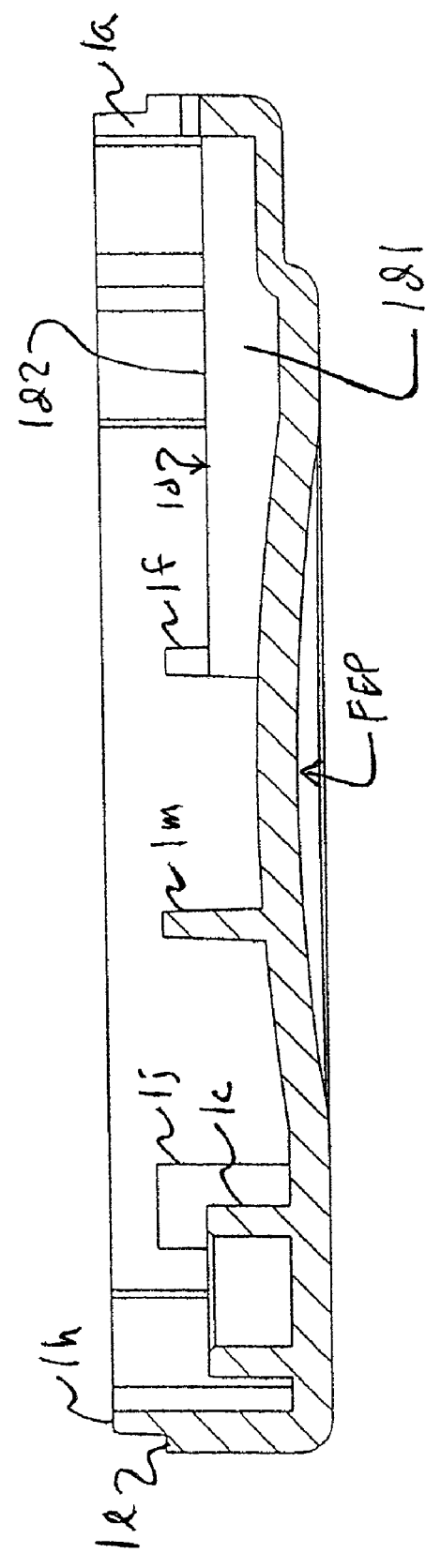
FIG. 7 shows a side cross-section view of FIG. 4.

The lower body part 1 preferably has a front portion 1e which has a smaller cross-section than the main portion of the part 1. The purpose of this smaller cross-section front portion is to allow the protecting cap PC to be easily installed thereon (see FIGS. 1-3) without significantly increasing an overall width, length and thickness of the lancet device LD. The lower body part 1 also preferably has, with the exception of portion 1e and the indented finger gripping portion FEB, a generally planar inner surface 1i which extends between the generally straight side walls. The lower body part 1 additionally preferably includes two plate-like guiding projections or ribs 1d which are generally centrally disposed relative to the side walls. The inner surfaces 1d1 of these spaced apart substantially parallel projections 1d are sized to movably engage the planar sides 6e of the slide member 6. The upper surfaces 1d2 of these spaced apart projections 1d are designed to movably engage with planar surfaces 6b of the slide member 6. The purpose of these spaced-apart plate-like projections 1d is to guide the slide member 6 and the front portion of the blade member 5 back and forth along a generally linear path (see e.g., FIGS. 25-27). Additional plate-like projections 1g extend perpendicularly from the projections 1d. These projections 1g have an upper surface which is arranged at the same height as the projections 1d. As a result, the projections 1g provide a support surface for the arms 3b and 3c and, together with projections 1d and projections 2c, provide surfaces which both supports the trigger cap 3 and helps guide the movement of the trigger cap 3 relative to the lancet body. As can be seen in FIGS. 4-6, the lower housing part 1 also includes a projection 1b which is positioned adjacent the right side wall. The projection 1b serves as an anchor for one end of the spring 4 (see e.g., FIG. 24). The projection 1b extends up past the upper edge 1h of the lower housing part by approximately 3 mm and substantially extends to the inner surface 2d of the upper housing part 2, thereby preventing the inadvertent disengagement of the spring 4. The lower housing part 1 also includes a tubular projection 1c whose central opening is sized to receive therein (with a small clearance) the circular projection 7b of the connecting part 7. This movable connection allows the connecting member 7 to pivot or rotate about a center axis of the tubular projection 1c (see e.g., FIGS. 24-27). The lower housing part 1 further includes a stop projection 1j which is positioned to limit the counterclockwise movement of the connecting member 7 when the trigger cap 3 is moved from an initial position (see e.g., FIG. 24) to another position prior to causing the triggering of the lancet device (see e.g., FIG. 25). The lower housing part 1 also includes, by way of non-limiting example, four openings 1k which are sized to frictionally engage and receive therein four similarly spaced projections 2g of the upper housing part 2. The lower housing part 1 further also includes two spaced apart plate-like stop projections 1f which extend above the surfaces 1d2. These projections 1f are positioned to engage the ends of the arms 3b and 3c and act to limit the inward movement of the trigger cap 3 during the triggering of the lancet device LD. Finally, the lower housing part 1 has a stiffening support rib 1m which supports the blade member 5 during its movement and also utilizes a peripheral shoulder 1l which is sized and shaped to engage with the peripheral edge 2f of the upper housing part 2.

Figure 8:
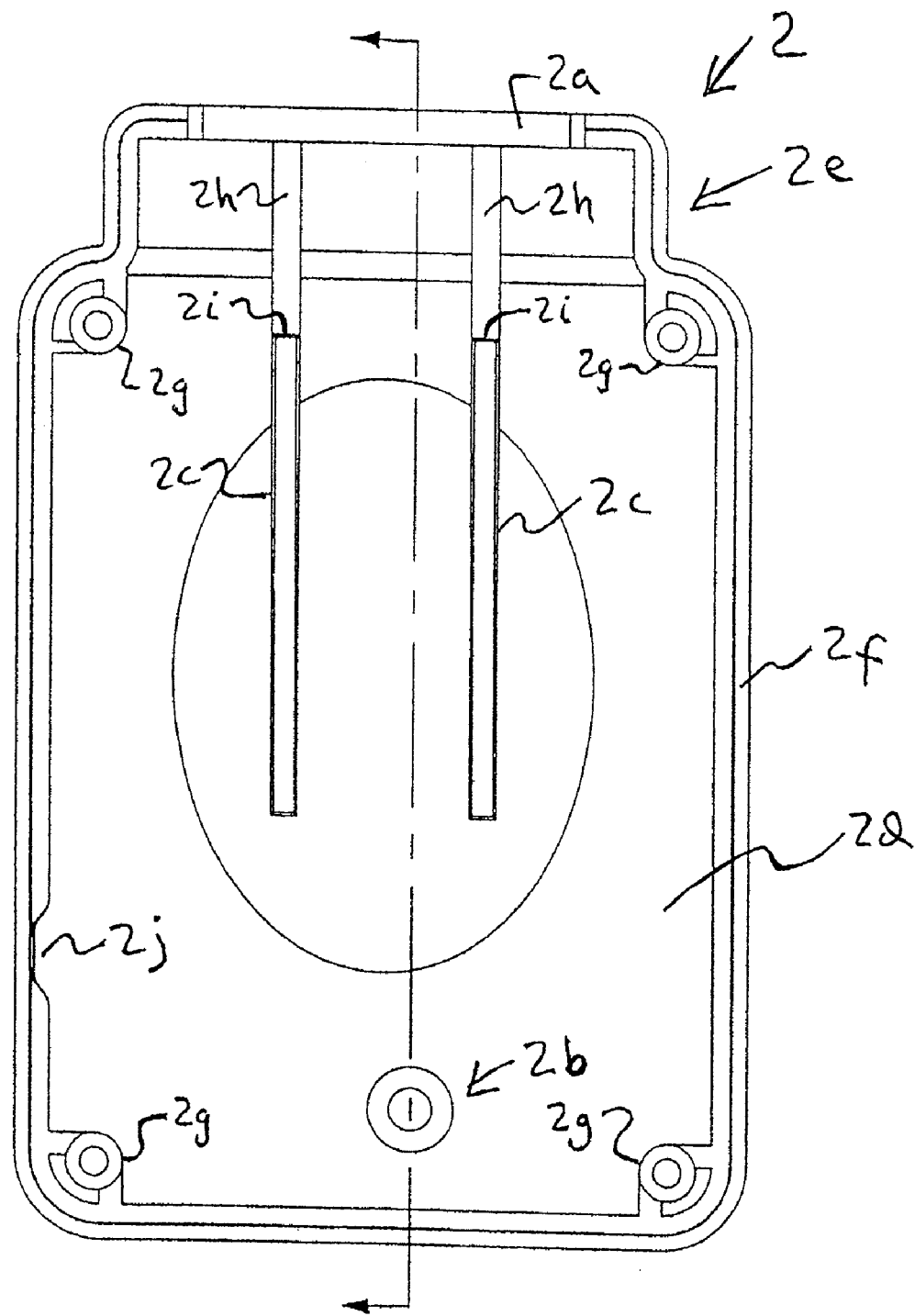
FIG. 8 shows an inside view of the upper housing part of the embodiment shown in FIG. 1.
Figure 9:
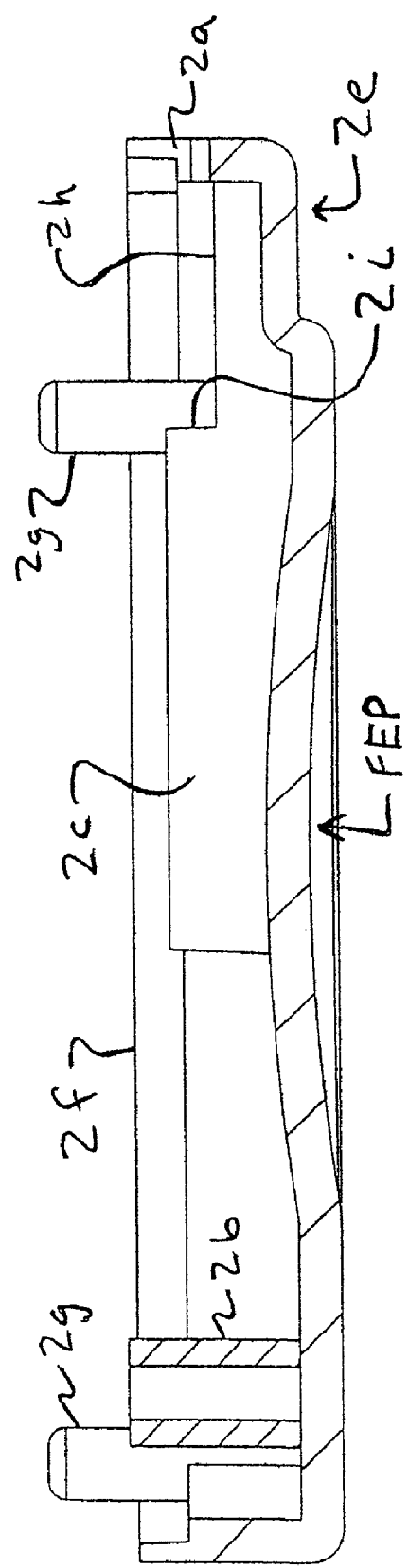
FIG. 9 shows a side cross-section view of FIG. 8.
Figure 10:
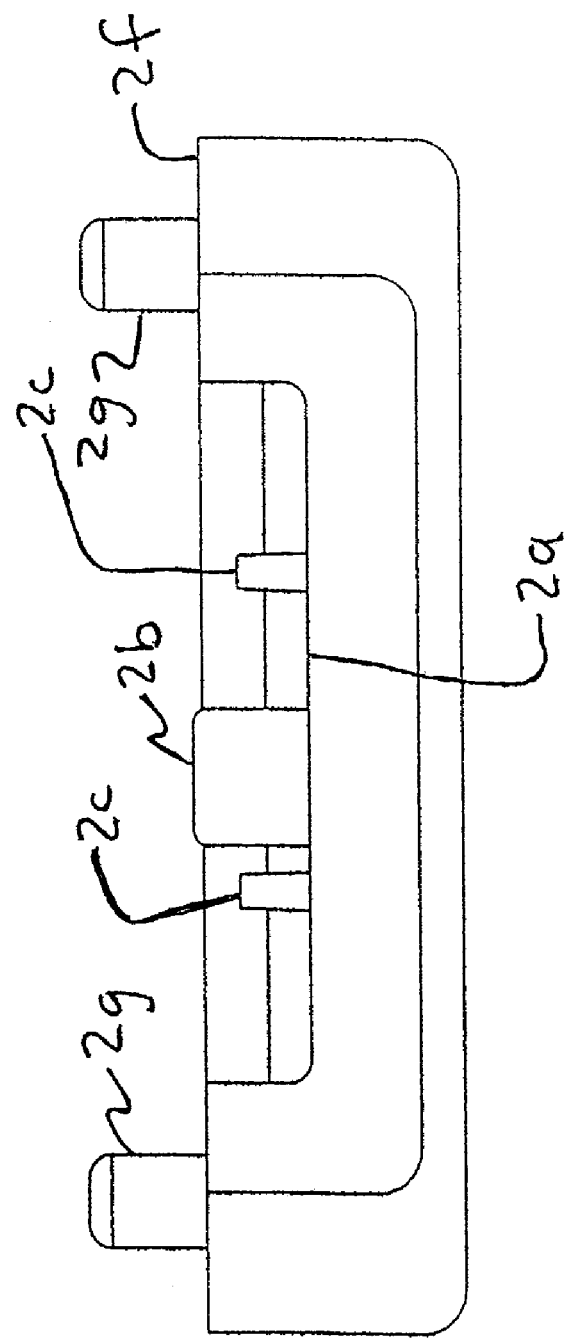
FIG. 10 shows a top view of the upper housing part of FIG. 8.

With reference to FIGS. 8-10, it can be seen that the front body or upper housing part 2 can preferably be made as one-piece structure by e.g., injection molding. In this regard, it is preferably made of a plastic or synthetic resin such as, e.g., ABS plastic. The upper body part 2 may also be made of ABS—Metallic Silver and have a finish designated as SPI-A2. Of course, other materials and/or finishes may be utilized, without leaving the scope of the invention. Additionally, the upper body part 2 may have an overall length (measured vertically across FIG. 8) that is approximately 40 mm and an overall width (measured horizontally across FIG. 8) of approximately 26 mm. Although undesirable for reasons of cost, the upper body part 2 may even be made of a plurality of sections of parts which are joined together to form the complete upper body part 2, without leaving the scope of the invention.

The upper body part 1 preferably has a front portion 2e which has a smaller cross-section than the main portion of the part 2. The purpose of this smaller cross-section front portion is to allow the protecting cap PC to be easily installed thereon (see FIGS. 1-3) without significantly increasing an overall width, length and thickness of the lancet device LD. The upper body part 2 also preferably has, with the exception of portion 2e and the indented finger gripping portion FEB, a generally planar inner surface 2d which extends between the generally straight side walls. The upper body part 2 additionally preferably includes two plate-like guiding projections or ribs 2c which are generally centrally disposed relative to the side walls. The upper surfaces of these spaced apart substantially parallel projections 2c are arranged to movably engage the upper side 5d of the blade member 5. The lower surfaces 2h of these spaced apart projections 2c are designed to movably engage with planar surface 3d of the trigger cap 3. A shoulder 2i is provided on each projection 2c and is utilized to engage edge 3e of the trigger cap 3 to limit maximum inward movement of the trigger cap 3 into the lancet device LD. As can be seen in FIGS. 8-10, the upper housing part 2 also includes a projection 2b which is positioned such that its center axis is substantially aligned with the center axis of the tubular projection 1c so that when the housing parts 1 and 2 are connected together, the projections 1c and 2b act to axially constrain the axial movement of the connecting member 7, while also allowing rotational movement of the connecting member 7 about the axes of the projections 1c and 2b. The upper housing part 2 also includes an inwardly curved indentation 2j on the inner portion of the left side wall. This indentation 2j, together with the projection 1b, serve to secure one end of the spring 4 (see e.g., FIG. 24). The upper housing part 2 also includes, by way of non-limiting example, four projections 2g which extend approximately 3 mm above edge 2f and which are sized to frictionally engage and penetrate four similarly spaced openings 1k of the lower housing part 1. Finally, the upper housing part 2 utilizes a peripheral edge 2f which is sized and shaped to engage with the peripheral shoulder 1l of the lower housing part 1 when the upper and lower housing parts 2, 1 are connected/assembled together.

With reference to FIGS. 11-14, the lancet blade member 5 can be a stainless steel one-piece stamped member substantially covered or coated with a plastic material such as e.g., ABS, and whose tip portion 5a is shaped with an angled sharpened edge 5b. The blade member 5 also includes a front edge portion 5c and a generally rectangular-shaped body portion. The front side 5d of the blade member 5 has one projection 5e which is designed to receive one end of the spring 4 and a rear side 5f having two projections 5g and 5h. The blade member 5 can also optionally include a D-shaped through opening 5i. By way of non-limiting example, the blade member 5 can have a thickness of between approximately 1 mm and approximately 1.5 mm. The overall length of the blade member can be approximately 33.37 mm and the width can be approximately 9 mm. As is exemplified in the second embodiment, the projection 5h is sized to be received in opening 6a of the slide member 6. The other projection 5g is similarly sized to be received in opening 7a of the connecting member 7. A small clearance is provided between these projections 5g, 5h and openings 6a, 7a so as to allow unimpeded rotational and/or pivoting movement of the connecting member 7 relative to a rear portion of the blade member 5 and to allow unimpeded rotational and/or pivoting movement of a front portion of the blade member 5 relative to the slide member 6 (see e.g., FIGS. 24-27). As explained above, the front surface 5d is designed to movably engage the upper surfaces of the two ribs 2c of the upper housing part 2.

Although not shown, the embodiment of FIGS. 1-23 utilizes a spring 4 similar to the spring 4 used in the embodiment shown in FIGS. 24-27. In this regard, the spring 4, which can be made of spring steel and which can have the form of a helical coil spring, has one end coupled to the projection 5e of the blade member 5 and another end coupled to projection 1b of the lower housing part 1. This spring 4 causes (and/or biases) the trigger cap 3 towards an extended position, i.e., an initial prior-use position before the trigger cap 3 is activated. This occurs because the spring 4 wants to move the rear end of the blade member 5 to the right (see FIG. 24) but is prevented from doing so because of engagement between angled surfaces 3b1 and 3c1 of the deflecting arms 3b and 3c and the angled surfaces 6d of the slide member 6. However, when sufficient force is applied to the trigger cap 3 so as to cause the deflecting arms 3b and 3c to deflect or bend away from each other due to engagement with surfaces 6d of the slide member 6, a point in the movement will be reached when the arms reach hill portions 6g. Any further movement past this point will allow the arms 3b and 3c to move towards each other and will allow the spring 4 to move the rear portion of the blade member 5 to the right. This movement, however, will be along a curved path owing to the fact that the connecting member 7 has one end 7d rotatably connected to the projection 5g and another end 7b rotatably connected to an opening of a projection 1c of the lower housing part. The movement of the front portion of the blade member 5 will have both a linear component, due to the linear movement of the slide member 6 as guided by the two guiding ribs 1d, and a curved component due to the pivoting or rotation of the projection 5h and in the opening 6a of the slide member 6. Such movement will, of course, occur very rapidly, i.e., in a fraction of a second and is shown, by way of the example, in FIGS. 24-27.

Figure 15:
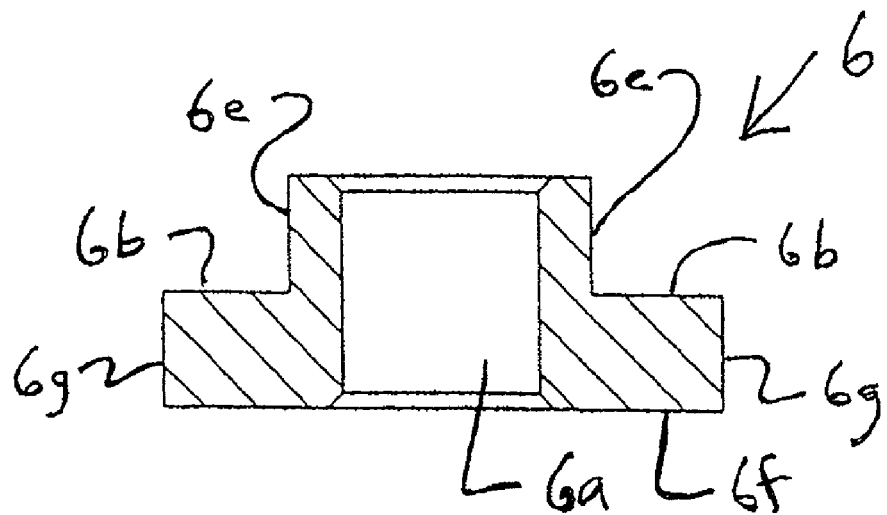
FIG. 15 shows a cross-section view of the slide member shown in FIG. 16 and used in the embodiment shown in FIG. 1.
Figure 16:
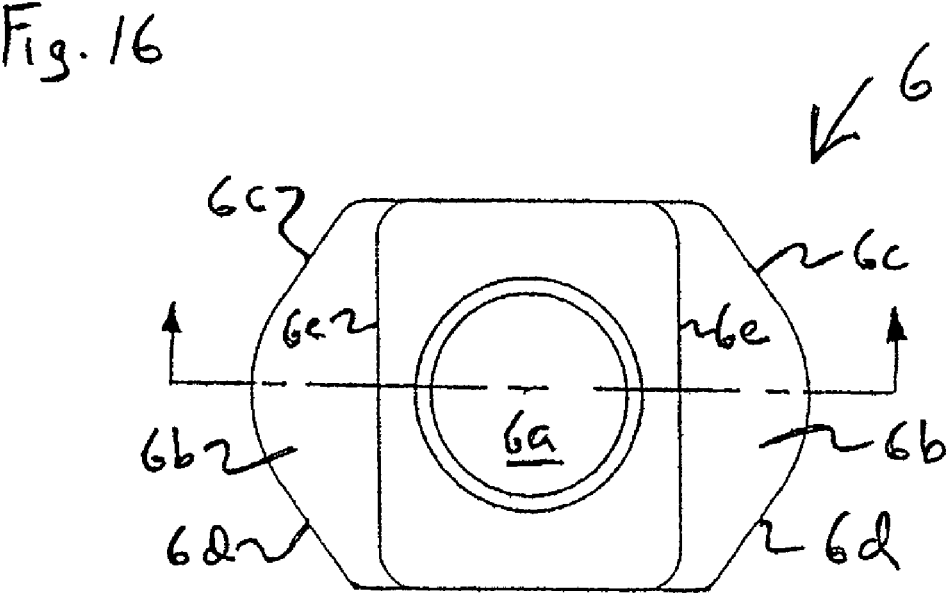
FIG. 16 shows a rear view of the slide member shown in FIG. 15.

FIGS. 15 and 16 show various views of the slide member 6. The slide member 6 can preferably be made as one-piece structure by e.g., injection molding. In this regard, it is preferably made of a plastic or synthetic resin such as, e.g., ABS plastic. The slide member 6 may also be made of ABS—red and have a finish designated as SPI-A2. Of course, other materials and/or finishes may be utilized, without leaving the scope of the invention. Additionally, by way of non-limiting example, the slide member 6 may have an overall length that is approximately 7.4 mm (measured horizontally across FIG. 15), and over width of approximately 5 mm (measured vertically in FIG. 16), and an overall thickness of approximately 2.4 mm. Moreover, the slide member 6 may even be made of a plurality of sections of parts which are joined together to form the complete slide member 6, without leaving the scope of the invention, although it is preferred that it be formed a one-piece member. It would be even more preferable if the slide member 6 were integrally formed with the lancet body, and in particular, integrally formed with the lower body part 1 and connected thereto with a living hinge (not shown).

As explained above, the slide member 6 has two generally parallel planar sides 6e which are designed to slidably engage with the inner surfaces 1d1 of the ribs 1d and a central opening 6a which is sized to receive therein the front projection 5h of the blade member 5. The generally planar surfaces 6b of the slide member 6 slidably engage upper surfaces 1d2 of the ribs 1d. An upper surface 6f of the slide member contacts the lower surface 5f of the blade member 5 when the slide member 6 is installed on the blade member 5. Forward angled surfaces 6d of the slide member 6 are designed to frictionally slidably engage with angled surfaces 3b1 and 3c1 of the arms of the trigger cap 3 when the trigger cap 3 is in the initial pre-triggered position (see e.g., FIG. 24). Rear angled surfaces 6c of the slide member 6 are designed to frictionally engage with projections 3b2 and 3c2 of the arms 3b, 3c of the trigger cap 3 when the trigger cap 3 is in the post-triggered position (see e.g., FIG. 27).

Figure 17:
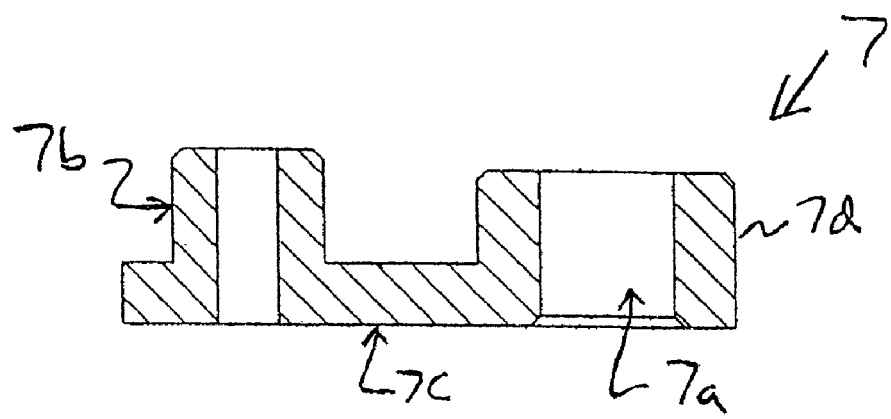
FIG. 17 shows a cross-section view of the connecting member shown in FIG. 18 and used in the embodiment shown in FIG. 1.
Figure 18:
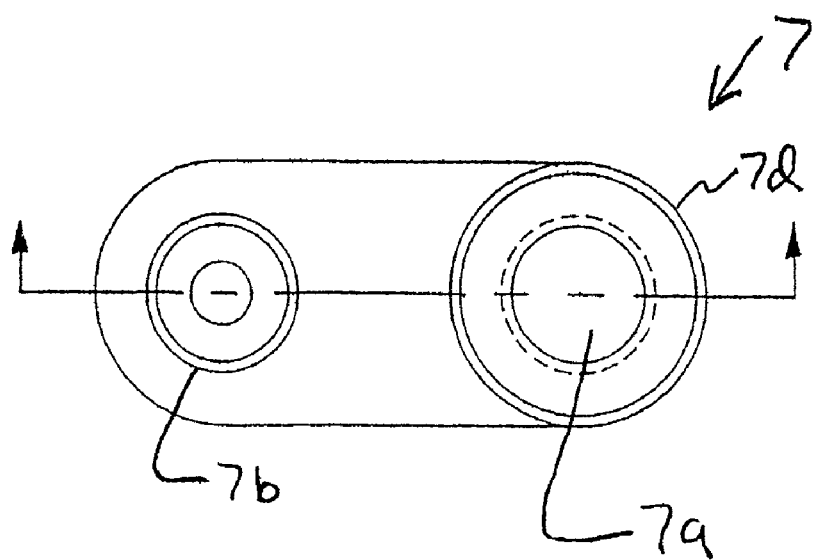
FIG. 18 shows a rear view of the connecting member shown in FIG. 17.

FIGS. 17 and 18 show various views of the connecting member 7. The connecting member 7 can preferably be made as one-piece structure by e.g., injection molding. In this regard, it is preferably made of a plastic or synthetic resin such as, e.g., ABS plastic. The connecting member 7 may also be made of ABS—red and have a finish designated as SPI-A2. Of course, other materials and/or finishes may be utilized, without leaving the scope of the invention. Additionally, by way of non-limiting example, the connecting member 7 may have an overall length that is approximately 11.6 mm (measured horizontally across FIG. 17), and over width of approximately 5 mm (measured vertically in FIG. 18), an overall thickness of projection 7b of approximately 4 mm, and an overall thickness of projection 7d of approximately 3 mm. Moreover, the connecting member 7 may even be made of a plurality of sections of parts which are joined together to form the complete connecting member 7, without leaving the scope of the invention, although it is preferred that it be formed a one-piece member. It would be even more preferable if the connecting member 7 were integrally formed with the lancet body, and in particular, integrally formed with the lower body part 1 and connected thereto with a living hinge (not shown).

As explained above, the connecting member 7 has a generally planar upper side 7c which is designed to slidably engage with bottom surface 5f of the blade member 5 when the rear projection 5g is fully inserted into the opening 7a. The circular projection 7b rotatably engages the central opening in the tubular projection 1c. The connecting member 7 thus forms connecting link with two pivot/rotatable connection points, i.e., one formed by the projection 7b and the opening of projection 1c of the lower housing 1, and another formed by the opening 7a and projection 5h of the blade member 5.

FIGS. 19-21 show various views of the trigger cap 3. The trigger cap 3 can preferably be made as one-piece structure by e.g., injection molding. In this regard, it is preferably made of a plastic or synthetic resin such as, e.g., ABS plastic. The trigger cap 3 may also be made of ABS—red and have a finish designated as SPI-A2. Of course, other materials and/or finishes may be utilized, without leaving the scope of the invention. Additionally, by way of non-limiting example, the trigger cap 3 may have an overall length that is approximately 13.3 mm (measured from surface SCS to the ends of arms 3b and 3c), and over width of approximately 17.3 mm (measured across the shoulders 3a), and an overall thickness of approximately 4.2 mm. Moreover, the trigger cap 3 may even be made of a plurality of sections of parts which are joined together to form the complete trigger cap 3, without leaving the scope of the invention, although it is preferred that it be formed a one-piece member. It would be even more preferable if the trigger cap 3 were integrally formed with the lancet body, and in particular, integrally formed with the lower body part 1 and connected thereto with a living hinge (not shown).

As explained above, the trigger cap 3 has two generally parallel planar sides 3d and 3f. Upper surface 3d is designed to slidably engage with the upper surfaces 2h of the upper housing 2 and lower surface 3f is designed to slidably engage with upper surfaces 1d2 of the ribs 1d as well as upper surfaces of the ribs 1g. The generally parallel arms 3b, 3c include angled surfaces 3b1, 3c1 and inward facing projections 3b2, 3c2. The angled surfaces 3b1 and 3c1 are designed to frictionally slidably engage with angled surfaces 6d of the slide member 6 when the trigger cap 3 is in the initial pre-triggered position (see e.g., FIG. 24). Projections 3b2 and 3c2 of the arms 3b, 3c frictionally engage the rear angled surfaces 6c of the slide member 6 when the trigger cap 3 is in the post-triggered position (see e.g., FIG. 27). By way of non-limiting example, the blade receiving opening BO can have a rectangular configuration as is shown in FIG. 19, with the width being significantly larger than the height. Other shapes are also contemplated for the opening BO.

Figure 23:
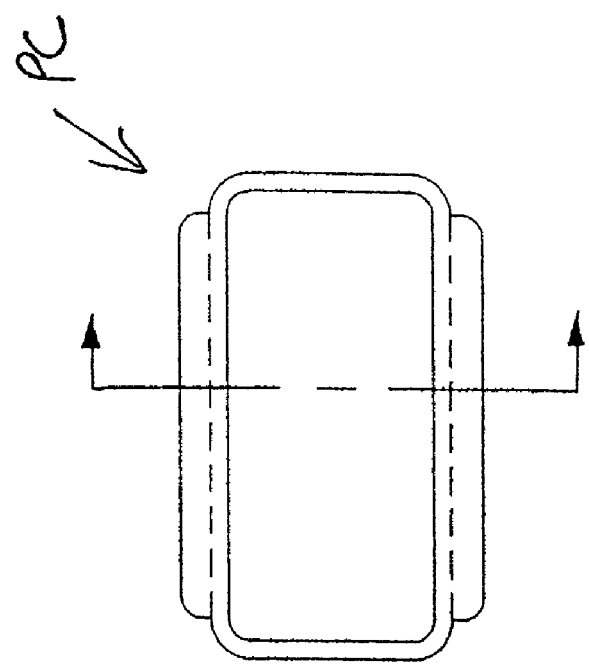
FIG. 23 shows a top view of the protective cap shown in FIG. 22.
Figure 22:
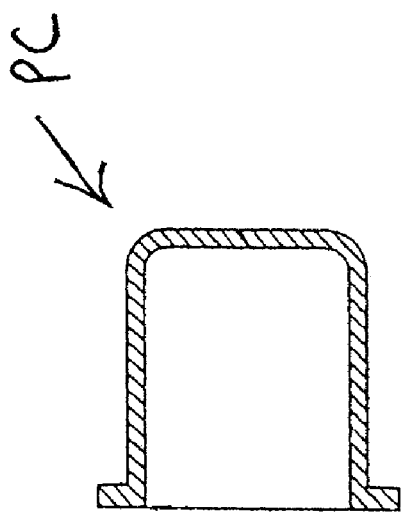
FIG. 22 shows a cross-section of the protective cap shown in FIG. 23 and used in the embodiment shown in FIG. 1.

FIGS. 22-23 show various views of the protective cap PC. The cap PC can preferably be made as one-piece structure by e.g., injection molding. In this regard, it is preferably made of a plastic or synthetic resin such as, e.g., ABS plastic. The cap PC may also be made of ABS—red and have a finish designated as SPI-A2. Of course, other materials and/or finishes may be utilized, without leaving the scope of the invention. Additionally, by way of non-limiting example, the cap PC may have an overall thickness that is approximately 12.3 mm (measured horizontally in FIG. 22), and an overall width of approximately 13.6 mm (measured vertically in FIG. 23), and an overall length of approximately 21.7 mm (measured horizontally in FIG. 23). Moreover, the cap PC may even be made of a plurality of sections of parts which are joined together to form the complete cap PC, without leaving the scope of the invention, although it is preferred that it be formed a one-piece member. It would be even more preferable if the cap PC were integrally formed with the lancet body, and in particular, integrally formed with the lower body part 1 and connected thereto with a living hinge (not shown). As explained above, the cap PC has generally parallel planar sides whose inner surfaces are designed to frictionally engage portions 1e/2e of the body parts.

The operation of the device shown in FIGS. 1-23 will now be explained with reference to the second embodiment shown in FIGS. 24-27. Although the first embodiment is different from the second embodiment, the differences mainly relate to the configuration of the front portion of the housing parts and also that the configuration of the slide member guiding ribs of the lower housing part, and also related to the fact that the upper and lower housing parts can be transparent and/or translucent. The operation of both devices is, however, substantially similar. Thus, FIG. 24 shows the position of the trigger cap TC prior to the lancet device LD being used. In this position, the blade member BM is in a first retracted position, the spring 4 applies a tension, the connecting member CM is rotated to the 11 O'clock position, and the front angled surfaces of the slide member SM are in engagement with the angled surfaces of the arms of the trigger cap TC. FIG. 25 shows the position of the trigger cap TC just after a force F is applied thereto, as will generally occur when the trigger cap TC is pressed against a user's skin. In this position, the trigger cap TC has moved inwardly and caused the slide member SM to move down, which in turn has caused the blade member BM to move to another even more retracted position limited by contact between the connecting member CM and a projection fixed to the body. In this additional retracted position, the spring 4 becomes more elongated and tensioned, the connecting member CM is rotated to the 10 O'clock position, and the front angled surfaces of the slide member SM continue to be engagement with the angled surfaces of the arms of the trigger cap TC. FIG. 26 shows the position of the trigger cap TC just after an even greater force F is applied thereto, as will generally occur when the trigger cap TC is pressed sufficiently against a user's skin to cause automatic triggering of the lancet device LD. In this position, the trigger cap TC has moved inwardly to its fullest extent. Because the blade member BM and the projection have prevented further inward movement of the slide member SM, the arms of the trigger cap TC have been forced apart as they pass to angled surfaces 6c. This movement releases the slide member SM from engagement with the arms of the trigger cap TC and allows the spring 4 to cause rear end of the blade member BM to rotate in the clockwise direction until it reaches the position shown in FIG. 27. However, as the blade member BM moves from the position of FIG. 25 to the position of FIG. 27, it moves past the position shown in FIG. 26 thereby allowing the tip of the blade member BM to penetrate a user's skin. In moving from the position of FIG. 26 to the position of FIG. 27, however, the blade member BM, under the action of the spring 4, moves the slide member SM inward until the rear angled surfaces engage the inward facing projections of the arms of the trigger cap TC thereby preventing the trigger cap TC from moving back out to the position shown in FIG. 24. The spring 4 also prevents the blade member BM from rotating counterclockwise which ensures that the tip of the blade member BM is not inadvertently caused to project outside of the blade opening. In the position of FIG. 27, the connecting member CM is rotated to the 2 O'clock position, and the rear angled surfaces of the slide member SM continue to be engagement with the inner projections of the arms of the trigger cap TC. The corresponding parts of the embodiment shown in FIGS. 24-27 can have similar and/or identical configurations/dimensions/materials as those described with regard to FIGS. 1-23, will not be described in detail herein.

FIGS. 28-67 show a third non-limiting preferred embodiment of a single-use and/or disposable blade lancet device LD. Lancet device LD has a lancet body made up of an upper or front body portion 20 and a lower or rear body portion 10. These parts 10 and 20 are connected to each other, e.g., using adhesives and/or fasteners and/or welding and/or snap-together holding mechanisms (not shown), when the lancet device LD is initially assembled. Preferably, the housing members 10 and 20 are connected together using projections and openings, as shown in the drawings. A blade member 50 (see FIGS. 41-43) is movably disposed within the body parts 10, 20 (e.g., in a manner similar to that shown in the embodiment of FIGS. 24-27). A front end cover or protective cap PC' (see also FIGS. 59-63) is removably connected or attached via, e.g., recesses R and projections P, to a front portion 10e/20e of the body parts 10, 20. The protective cap PC' can also be similar to the one exemplified in copending U.S. patent application Ser. No. 10/441,065 filed on May 20, 2003, the entire disclosure of which is hereby expressly incorporated by reference in its entirety.

The lancet device defines a plane or surface SCS which is, e.g., configured to contact (i.e., be positioned against) a user's skin. However, the instant embodiment may also utilize either an outwardly curved or an outwardly curved skin engaging surface SCS beyond which the tip portion 50a of the lancet blade member 50 (see FIGS. 41-44) can extend and/or project. Of course, the invention also contemplates using a planar front skin engaging surface SCS shown herein and also of the type described in, e.g., U.S. Pat. No. 6,258,112, the disclosure of which is hereby expressly incorporated by reference in its entirety.

Figure 28:
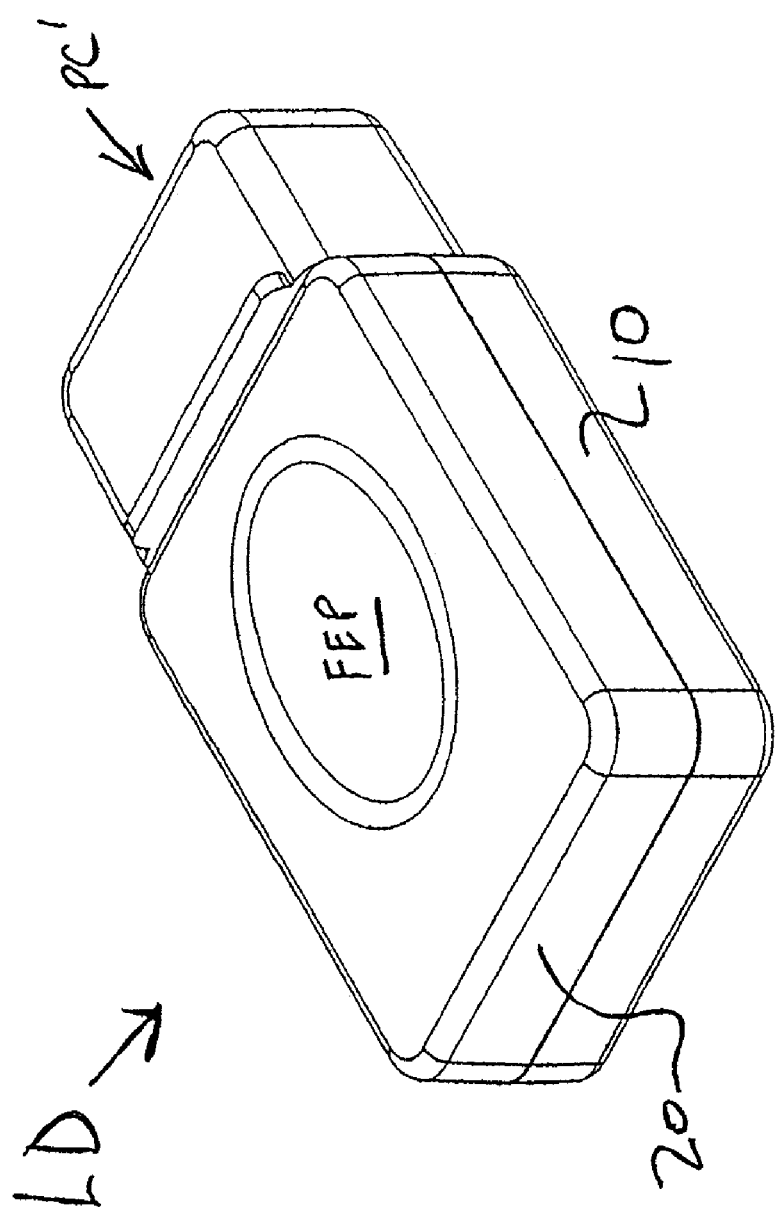
FIG. 28 shows a front view of still another embodiment of the disposable and single-use blade lancet device with the protective cap installed thereon.
Figure 30:
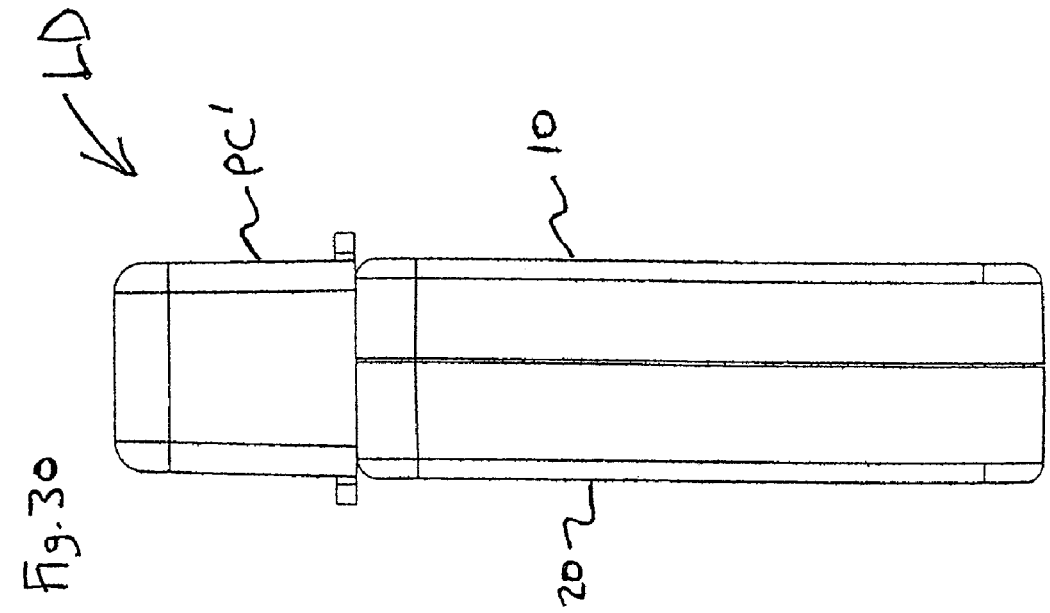
FIG. 30 shows a side view of the embodiment shown in FIG. 28.
Figure 29:
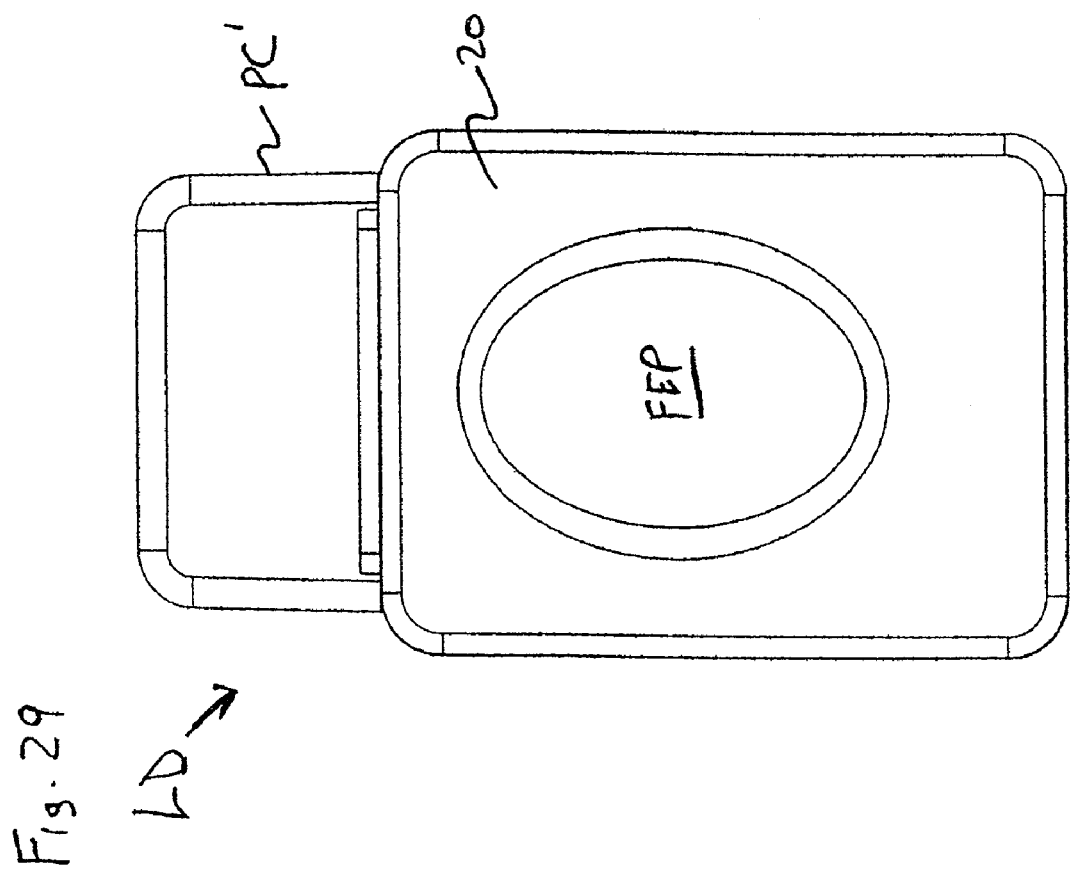
FIG. 29 shows a front view of the embodiment of FIG. 28.
Figure 36:
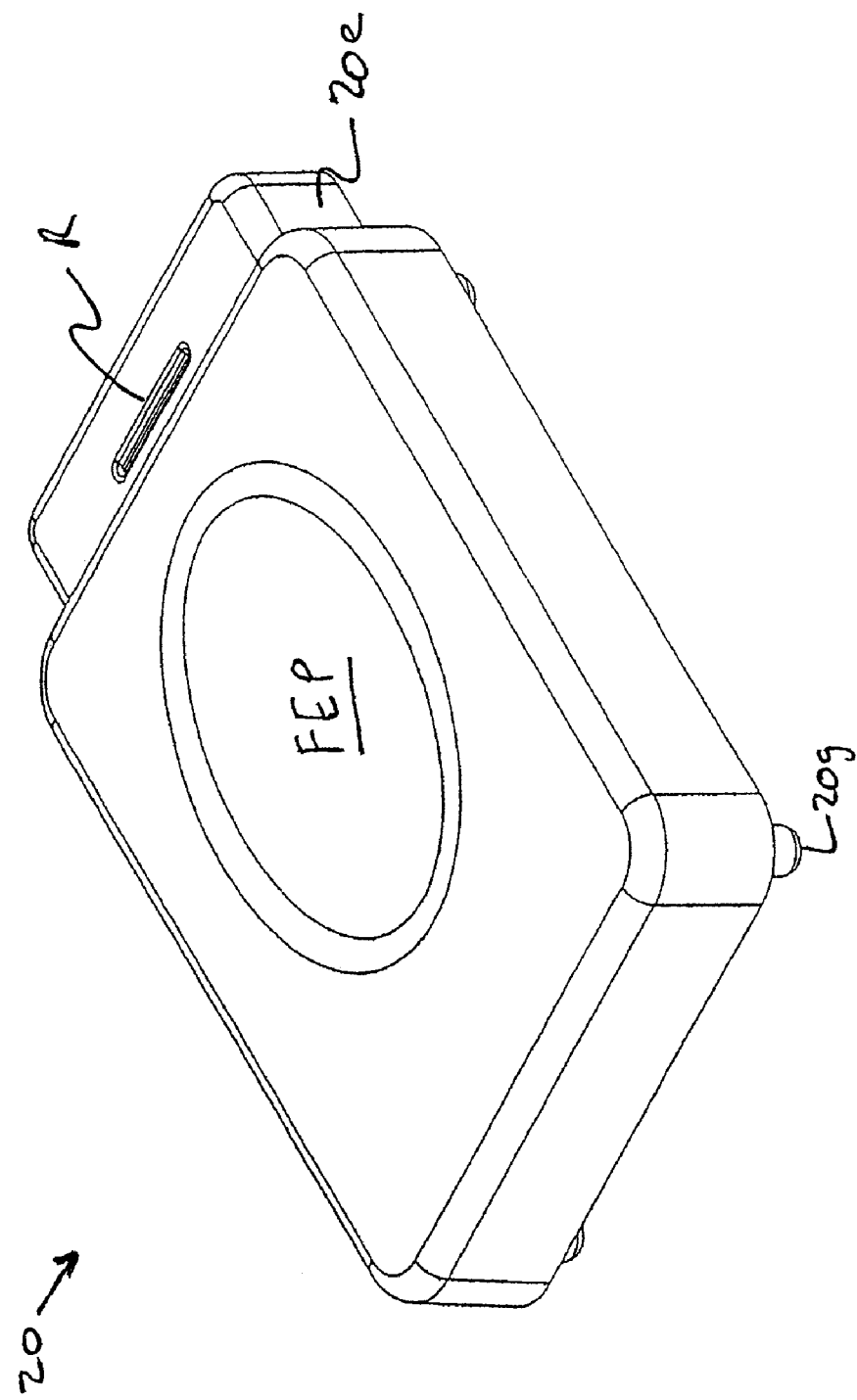
FIG. 36 shows a front perspective view of the upper housing part of the embodiment shown in FIG. 28.

As can be seen in FIGS. 28-30, the lancet body 20/10 can have a generally rectangular shape and can preferably also have an ergonomic shape to facilitate comfortable gripping/holding. Of course, the invention contemplates other shapes for the lancet body provided that they result in a relatively inexpensive design and/or which is economical to produce. As explained above, the front end of the lancet device LD includes a skin engaging surface SCS which is defined by outer surface of the trigger cap 30 (see FIGS. 54-58). A lancet blade opening BO' extends through an end wall of the trigger cap 30 and serves to allow the tip of lancet blade member 50 to penetrate beyond the surface SCS (see e.g., FIG. 26). In this regard, the trigger cap 30 is movably mounted to the front end portion of the lancet body. In the instant embodiment, the trigger cap 30 is a generally rectangular-shaped cap member for reasons of aesthetic design. However, the invention contemplates a variety of shapes for the trigger cap 30 such as, e.g., oval, triangular, square, polygonal, etc,. Moreover, in the instant embodiment, the trigger cap 30 is generally centrally mounted, relative to the sides of the lancet body. However, the invention contemplates other locations and/or positions for the trigger cap 30, provided such locations allow the lancet device to function properly. Other ways of associating the trigger cap 30 on the lancet body are expressly contemplated, such as, e.g., being integral with the housing and acting as a living hinge or spring. The trigger cap 30 is installed in an opening formed by partial openings 10a and 20a of the front cover 20 and rear cover 10 and is sized to slide within the opening 10a/20a in a smooth low-friction manner. As can be seen in FIGS. 54-58, the trigger cap 30 has shoulders 30a which engage inner surfaces of the opening 10a/20a (see e.g., FIG. 24) whereby the trigger cap 30 is prevented from falling out of the lancet body once installed. The trigger cap 30 is also sized to be slide intro and/or be pushed into the lancet body (see e.g., FIGS. 25 and 26). However, this movement is resisted owing to the fact that the trigger cap 30 is biased towards an extended position (see e.g., FIG. 24) via a torsion spring 40 and also by virtue of engagement between the slide member 60 and the deflecting arms 30b and 30c. This biasing force and engagement can be overcome, however, when the trigger cap 30 is pushed into the lancet body sufficiently (see e.g., FIGS. 25 and 26) by applying a force to the surface SCS. Furthermore, because the trigger cap 30 includes an opening BO', once triggered, the blade tip 50a will be allowed to pass there-through (see e.g., FIG. 26) in order to penetrate a user's skin. Moreover, because the trigger cap 30 also includes the deflecting arms 30b and 30c and, due to the tapered surfaces 60c and 60d, the trigger cap 30 is prevented from moving back to a pre-triggered position by the slide member 60, the blade member 50, the connecting member 70, and the spring 40. Thus, once triggered, the lancet device LD is automatically rendered unusable again—thereby rendering the device a single-use device, a safe device because the blade member 50 is safely contained in the housing, and a device which can be disposed of safely.

Although not shown, the lancet body can preferably includes a viewing opening. Alternatively, it can be made of a transparent/translucent material (see embodiment shown in FIGS. 24-27) so that the user can view the inner workings of the device and will be able to easily note that the device is properly set and/or has not be used. If a viewing opening or window is instead utilizes, it can be formed in the front cover 20 and can be arranged in a convenient area which allows the user to see the position of the blade member 50. The opening or window, of course, can have any desired shape or configuration and can be located at any desired location provided that the user is able to discern the setting position of the blade member 50. If a viewing window is utilized, it can preferable be in the area of the finger engaging/gripping portions or indentations FEP.

In the embodiment shown in FIGS. 28-67, the lancet device LD is designed to be procured and/or purchased in a pre-loaded arrangement (see FIGS. 28-30). In order to used the lancet device LD a single time, a user need only remove the protective cap PC' (which can be discarded) and, while gripping oppositely arranged ergonomic finger gripping portions FEP, and press the trigger cap 30 against the skin of a patient to use it. Once triggered, however, the user will be unable to use the device again owing to the fact that this embodiment, like the two previously described embodiments, contains no mechanism for forcing or moving the blade member 50 from the post-triggering or second retracted position shown in, e.g., FIG. 27, to the armed or first retracted position shown in, e.g., FIG. 24. Moreover, because, before triggering, the spring 40 maintains the blade member 50 in the first retracted position (see e.g., FIG. 24), the lancet blade member 50, and particularly the tip portion 50a, is kept safely within the lancet body. Furthermore, because, after triggering, the spring 40 maintains the blade member 5 in the second retracted position (see e.g., FIG. 27), the lancet blade member 50, and particularly the tip portion 50a, is also kept safely within the lancet body. Additionally, because of, after triggering, the engagement between the slide member 60 (and in particular surfaces 60c) and the arms 30b and 30c (and in particular surfaces 30b1 and 30c1) of the trigger cap 30, the user will be unable to move the trigger cap 30 back to the first retracted or pre-triggering position (see e.g., FIG. 24) and thereby prevent use the device again.

By way of non-limiting example, the armed position of the blade member 50, trigger cap 30, connecting member 70, slide member 60, and spring 40 can be set when the lancet device is manufactured and/or assembled, i.e., in a factory setting.

With reference to FIGS. 31-35, it can be seen that the rear body or lower housing part 10 can preferably be made as one-piece structure by e.g., injection molding. In this regard, it is preferably made of a plastic or synthetic resin such as, e.g., ABS plastic. The lower body part 10 may also be made of ABS—Metallic Silver and have a finish designated as SPI-A2. Of course, other materials and/or finishes may be utilized, without leaving the scope of the invention. Additionally, the lower body part 10 may have an overall length (measured vertically across FIG. 33) that is approximately 40 mm and an overall width (measured horizontally across FIG. 33) of approximately 26 mm. Although undesirable for reasons of cost, the lower body part 10 may even be made of a plurality of sections of parts which are joined together to form the complete lower body part 10, without leaving the scope of the invention.

The lower body part 10 preferably has a front portion 10e which has a smaller cross-section than the main portion of the part 10. The purpose of this smaller cross-section front portion is to allow the protecting cap PC' to be easily installed thereon (see FIGS. 28-30) without significantly increasing an overall width, length and thickness of the lancet device LD. The lower body part 10 also preferably has, with the exception of portion 10e and the indented finger gripping portion FEB, a generally planar inner surface 10i which extends between the generally straight side walls. The lower body part 10 additionally preferably includes two plate-like guiding projections or ribs 10d which are generally centrally disposed relative to the side walls. The inner surfaces 10d1 of these spaced apart substantially parallel projections 10d are sized to movably engage the planar sides 60e of the slide member 60. The upper surfaces 10d2 of these spaced apart projections 10d are designed to movably engage with planar surfaces 60b of the slide member 60. The purpose of these spaced-apart plate-like projections 10d is to guide the slide member 60 and the front portion of the blade member 50 back and forth along a generally linear path (see e.g., FIGS. 25-27). Additional plate-like projections 10g extend perpendicularly from the projections 10d. These projections 10g have an upper surface which is arranged at the same height as the projections 10d. As a result, the projections 10g provide a support surface for the arms 30b and 30c and, together with projections 10d and projections 20c, provide surfaces which both supports the trigger cap 30 and helps guide the movement of the trigger cap 30 relative to the lancet body. As can be seen in FIGS. 31 and 33 the lower housing part 10 also includes a projection 10c which serves as a support for the opening of the torsion spring 40 (see e.g., FIGS. 64-66). The projection 10c extends up from the inner surface 10i of the lower housing part 10 by approximately 3 mm and substantially extends to the upper surface of projection 20b of the upper housing part 20, thereby preventing the inadvertent disengagement of the spring 40. The tubular projection 10c has a central opening sized to receive therein (with a small clearance) the circular projection 70b of the connecting part 70. This movable connection allows the connecting member 70 to pivot or rotate about a center axis of the tubular projection 10c (in a manner similar to that shown in, e.g., FIGS. 24-27). The lower housing part 10 further includes stop projections 10j and 10b. Stop projection 10j is positioned to limit the counterclockwise movement of the connecting member 70 when the trigger cap 30 is moved from an initial position (see e.g., FIG. 24) to another position prior to causing the triggering of the lancet device (see e.g., FIG. 25). Stop projection 10b is positioned to limit the clockwise movement of the connecting member 70 after the trigger cap 30 is moved to the post-triggered position (see e.g., FIG. 27). The lower housing part 10 also includes, by way of non-limiting example, four openings 10k which are sized to frictionally engage and receive therein four similarly spaced projections 20g of the upper housing part 20. The lower housing part 10 further also includes two spaced apart plate-like stop projections 10f which extend above the surfaces 10d2. These projections 10f are positioned to engage the ends of the arms 30b and 30c and act to limit the inward movement of the trigger cap 30 during the triggering of the lancet device LD. Finally, the lower housing part 10 has a stiffening support rib 10m which supports the blade member 50 during its movement and also utilizes a peripheral shoulder 10l which is sized and shaped to engage with the peripheral edge 20f of the upper housing part 20.

With reference to FIGS. 36-40, it can be seen that the front body or upper housing part 20 can preferably be made as one-piece structure by e.g., injection molding. In this regard, it is preferably made of a plastic or synthetic resin such as, e.g., ABS plastic. The upper body part 20 may also be made of ABS—Metallic Silver and have a finish designated as SPI-A2. Of course, other materials and/or finishes may be utilized, without leaving the scope of the invention. Additionally, the upper body part 20 may have an overall length (measured vertically across FIG. 38) that is approximately 40 mm and an overall width (measured horizontally across FIG. 38) of approximately 26 mm. Although undesirable for reasons of cost, the upper body part 20 may even be made of a plurality of sections of parts which are joined together to form the complete upper body part 20, without leaving the scope of the invention.

Figure 40:
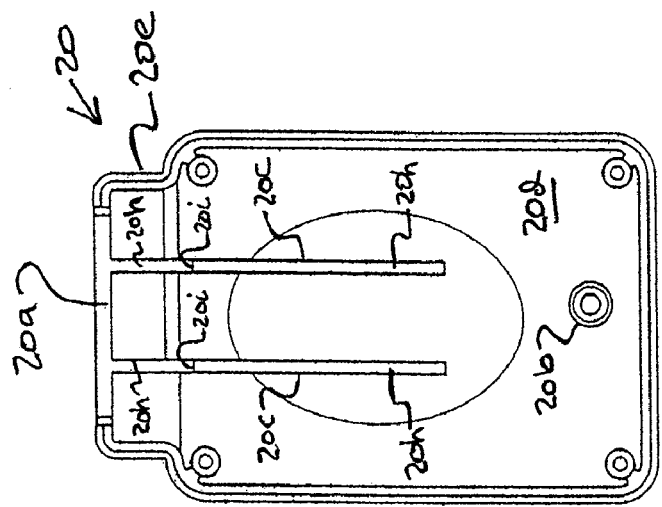
FIG. 40 shows an inside view of FIG. 36.
Figure 39:
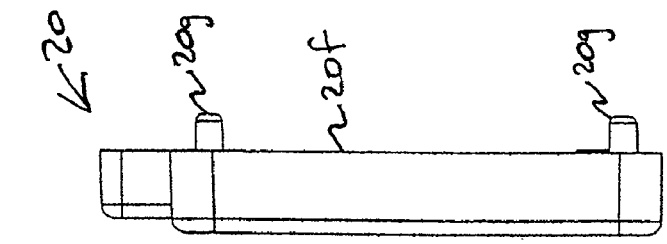
FIG. 39 shows a side view of FIG. 36.
Figure 37:
FIG. 37 shows a top view of FIG. 36.
Figure 38:
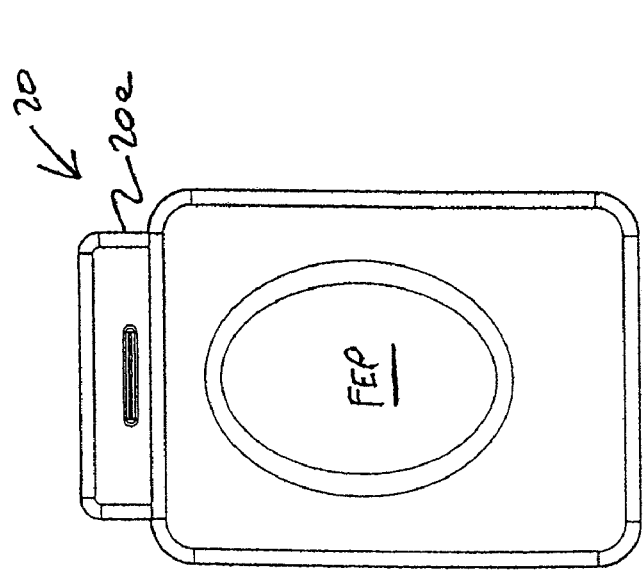
FIG. 38 shows a front view of FIG. 36.
Figure 61:
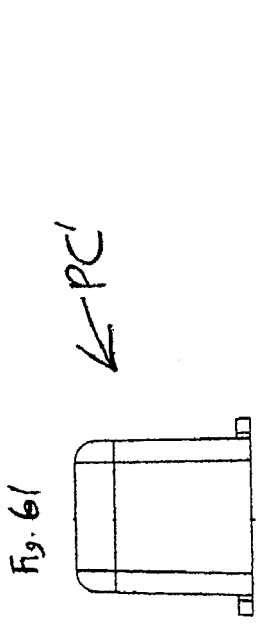
FIG. 61 shows a side view of the protective cap shown in FIG. 59.
Figure 62:
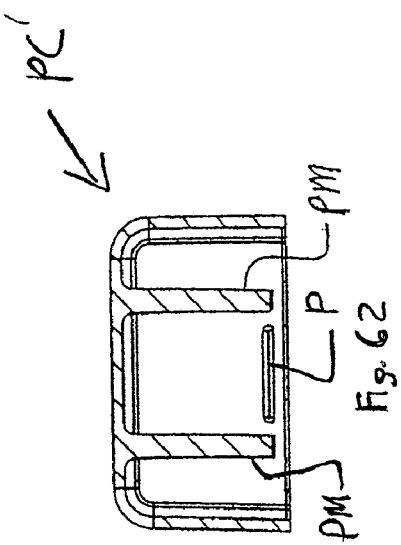
FIG. 62 shows a rear view of the trigger cap shown in FIG. 59.
Figure 59:
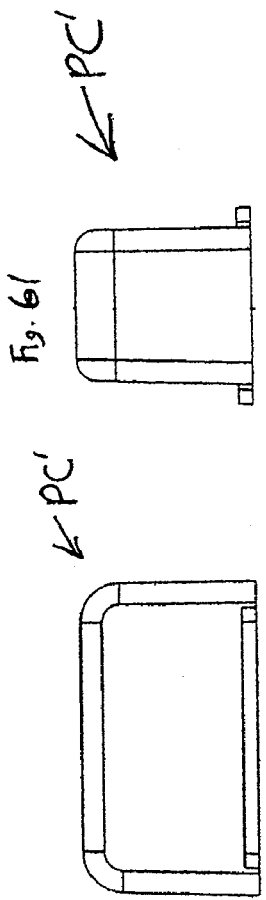
FIG. 59 shows a front view of the protective cap used in the embodiment shown in FIG. 28.
Figure 60:
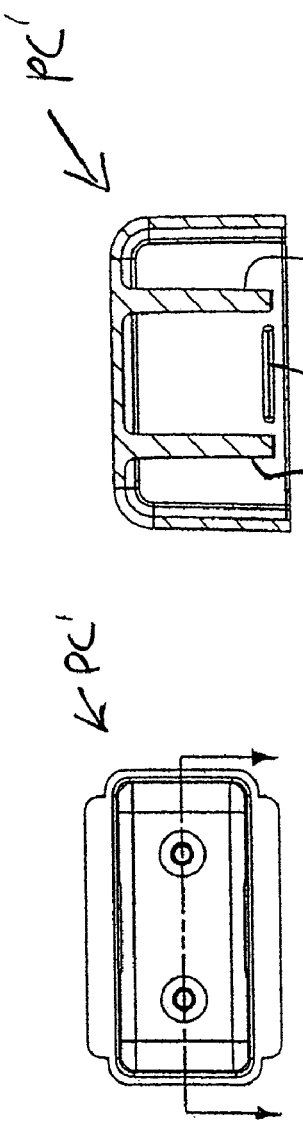
FIG. 60 shows an inside bottom end view of the protective cap shown in FIG. 59.
Figure 63:
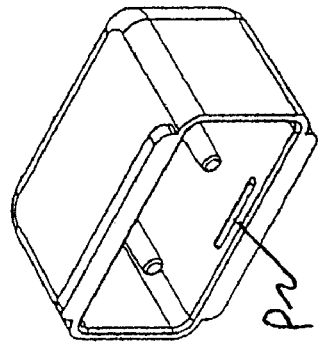
FIG. 63 shows a front perspective view of the protective cap shown in FIG. 59.
Figure 64:
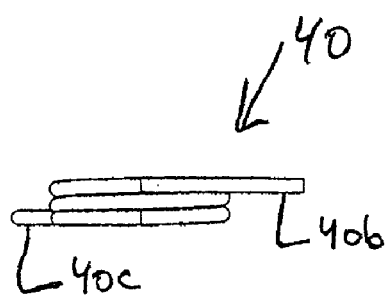
FIG. 64 shows a side view of the torsion spring used in the embodiment shown in FIG. 28.
Figure 65:
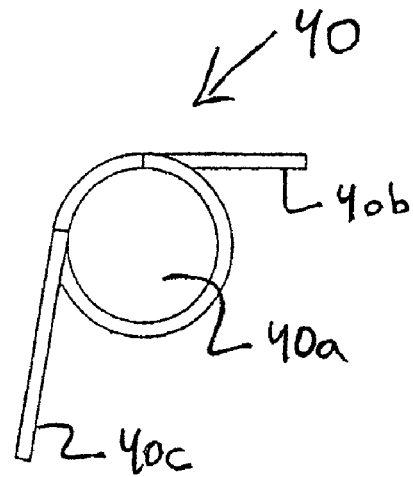
FIG. 65 shows a front view of the torsion spring shown in FIG. 64.
Figure 66:
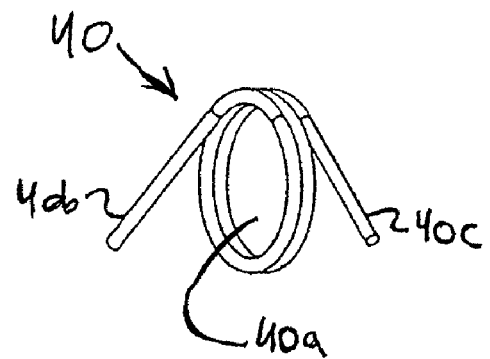
FIG. 66 shows a front perspective view of the torsion spring shown in FIG. 64.

The upper body part 10 preferably has a front portion 20e which has a smaller cross-section than the main portion of the part 20. The purpose of this smaller cross-section front portion is to allow the protecting cap PC' to be easily installed thereon (see FIGS. 28-30) without significantly increasing an overall width, length and thickness of the lancet device LD. The upper body part 20 also preferably has, with the exception of portion 20e and the indented finger gripping portion FEB, a generally planar inner surface 20d which extends between the generally straight side walls. The upper body part 20 additionally preferably includes two plate-like guiding projections or ribs 20c which are generally centrally disposed relative to the side walls. The upper surfaces of these spaced apart substantially parallel projections 20c are arranged to movably engage the upper side 50d of the blade member 50. The lower surfaces 20h of these spaced apart projections 20c are designed to movably engage with planar surface 30d of the trigger cap 30. A shoulder 20i is provided on each projection 20c and is utilized to engage edge 30e of the trigger cap 30 to limit maximum inward movement of the trigger cap 30 into the lancet device LD. As can be seen in FIGS. 37 and 40, the upper housing part 20 also includes a projection 20b which is positioned such that its center axis is substantially aligned with the center axis of the tubular projection 10c so that when the housing parts 10 and 20 are connected together, the projections 10c and 20b act to axially constrain the axial movement of the connecting member 70, while also allowing rotational movement of the connecting member 70 about the axes of the projections 10c and 20b. The upper housing part 20 also includes, by way of non-limiting example, four projections 20g which extend approximately 3 mm above edge 20f and which are sized to frictionally engage and penetrate four similarly spaced openings 10k of the lower housing part 10. Finally, the upper housing part 2 utilizes a peripheral edge 20f which is sized and shaped to engage with the peripheral shoulder 10l of the lower housing part 10 when the upper and lower housing parts 20, 10 are connected/assembled together.

With reference to FIGS. 41-44, the lancet blade member 50 can be a stainless steel one-piece stamped member substantially covered or coated with a plastic material such as e.g., ABS, and whose tip portion 50a is shaped with an angled sharpened edge 50b. The blade member 50 also includes a front edge portion 50c and a generally rectangular-shaped body portion. The front side 50d of the blade member 50 is generally planar surface. A rear side 50f having two projections 50g and 50h. The blade member 50 can also optionally include a D-shaped through opening 50i. By way of non-limiting example, the blade member 50 can have a thickness of between approximately 1 mm and approximately 1.5 mm. The overall length of the blade member can be approximately 33.37 mm and the width can be approximately 9 mm. As is exemplified in the second embodiment, the projection 50h is sized to be received in opening 60a of the slide member 60. Due to the fact that the projection 50h has deflecting portions, the projection 50h can be inserted into opening 60a and become axially connected to the slide member 60 via a snap connection. The other projection 50g is similarly sized to be received in opening 70a of the connecting member 70. A small clearance is provided between these projections 50g, 50h and openings 60a, 70a so as to allow unimpeded rotational and/or pivoting movement of the connecting member 70 relative to a rear portion of the blade member 50 and to allow unimpeded rotational and/or pivoting movement of a front portion of the blade member 50 relative to the slide member 60 (see e.g., FIGS. 24-27). As explained above, the front surface 50d is designed to movably engage the upper surfaces of the two ribs 20c of the upper housing part 20.

Figure 67:
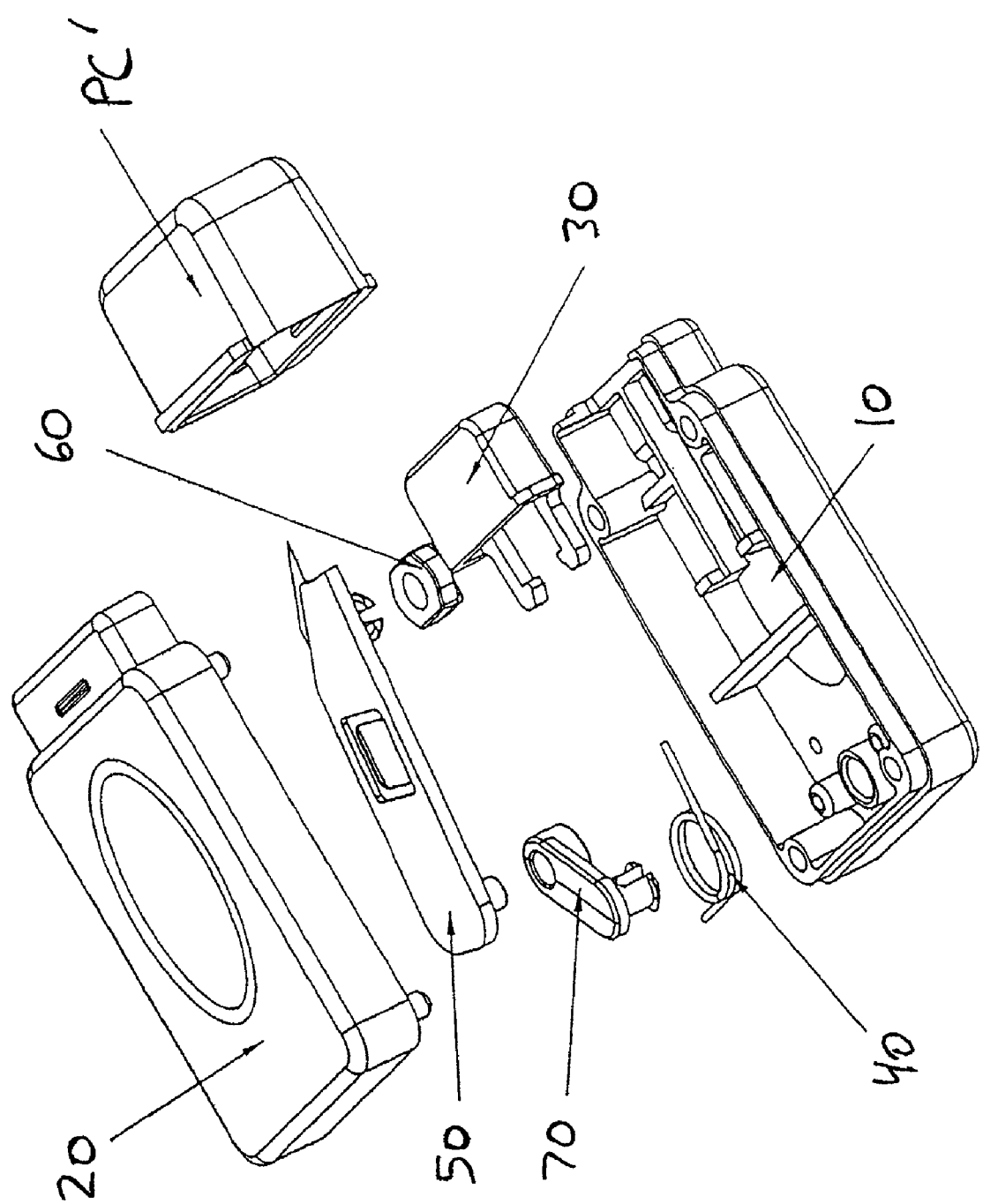
FIG. 67 shows the embodiment of FIG. 28 in a pre-assembled state.

As shown in FIG. 67, the embodiment of FIGS. 28-67 utilizes a spring 40 which is different than the spring 4 used in the embodiment shown in FIGS. 24-27. Of course, the invention contemplates using the extension spring 4 in place of the torsion spring 40 in the embodiment shown in FIGS. 28-67. In this regard, the spring 40, which can be made of spring steel and which can have the form of a torsion spring, has one end 40b which can be positioned between the projection 10j and the bottom wall of the lower housing part 10 and another end 40c which engages projection 70d. This spring 40 causes (and/or biases) the trigger cap 30 towards an extended position, i.e., an initial prior-use position before the trigger cap 30 is activated. This occurs because the spring 40 wants to move the rear end of the blade member 50 to the right (similar to that shown in FIG. 24) but is prevented from doing so because of engagement between angled surfaces 30b1 and 30c1 of the deflecting arms 30b and 30c and the angled surfaces 60d of the slide member 60. However, when sufficient force is applied to the trigger cap 30 so as to cause the deflecting arms 30b and 30c to deflect or bend away from each other due to engagement with surfaces 60d of the slide member 60, a point in the movement will be reached when the arms reach hill portions 60g. Any further movement past this point will allow the arms 30b and 30c to move towards each other and will allow the spring 40 to move the rear portion of the blade member 50 to the right. This movement, however, will be along a curved path owing to the fact that the connecting member 70 has one end 70d rotatably connected to the projection 50g and another end 70b rotatably connected to an opening of a projection 10c of the lower housing part 10. The movement of the front portion of the blade member 50 will have both a linear component, due to the linear movement of the slide member 60 as guided by the two guiding ribs 10d, and a curved component due to the pivoting or rotation of the projection 50h and in the opening 60a of the slide member 60. Such movement will, of course, occur very rapidly, i.e., in a fraction of a second and is shown, by way of the example, in FIGS. 24-27.

FIGS. 45-49 show various views of the connecting member 70. The connecting member 70 can preferably be made as one-piece structure by e.g., injection molding. In this regard, it is preferably made of a plastic or synthetic resin such as, e.g., ABS plastic. The connecting member 70 may also be made of ABS—red and have a finish designated as SPI-A2. Of course, other materials and/or finishes may be utilized, without leaving the scope of the invention. Additionally, by way of non-limiting example, the connecting member 70 may have an overall length that is approximately 11.6 mm (measured vertically in FIG. 46), and over width of approximately 5 mm (measured horizontally in FIG. 46), an overall thickness of projection 70b of approximately 4 mm, and an overall thickness of projection 70d of approximately 3 mm. Moreover, the connecting member 70 may even be made of a plurality of sections of parts which are joined together to form the complete connecting member 70, without leaving the scope of the invention, although it is preferred that it be formed a one-piece member. It would be even more preferable if the connecting member 70 were integrally formed with the lancet body, and in particular, integrally formed with the lower body part 10 and connected thereto with a living hinge (not shown).

Figure 68:
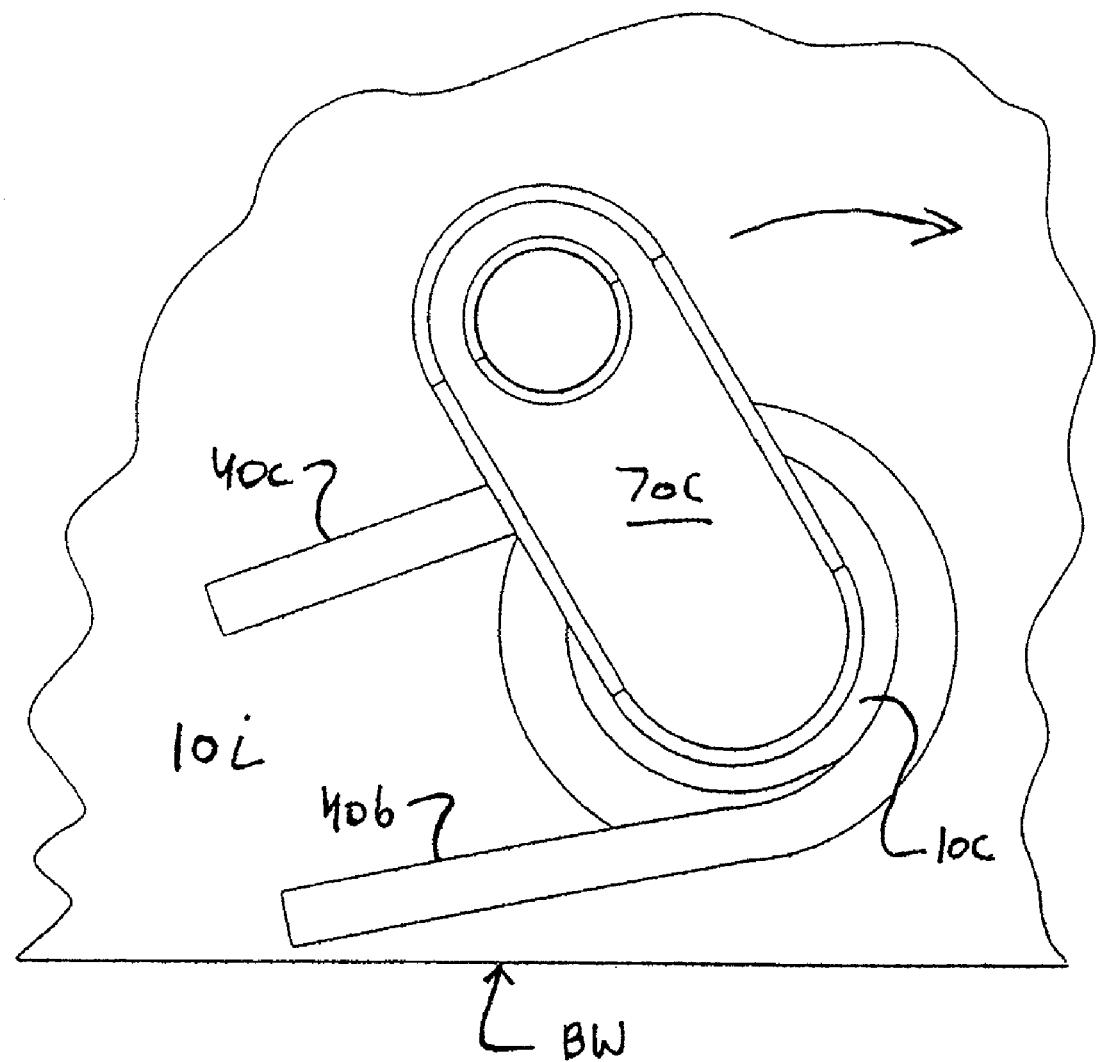
FIG. 68 shows one non-limiting way in which the torsion spring can be installed in the third embodiment.

As explained above, the connecting member 70 has a generally planar upper side 70c which is designed to slidably engage with bottom surface 50f of the blade member 50 when the rear projection 50g is fully inserted into the opening 70a. The circular projection 70b rotatably engages the central opening in the tubular projection 10c. The projection 70b also includes deflecting projections which provides a snap connection when inserted in the opening of the tubular projection 10c. This connection ensures that the connecting member 70 has limited axial movement while still allowing the connecting member 70 to rotate about an axis running through the tubular projection 10c. The connecting member 70 thus forms connecting link with two pivot/rotatable connection points, i.e., one formed by the projection 70b and the opening of projection 10c of the lower housing 10, and another formed by the opening 70a and the rear projection 50h of the blade member 50. FIG. 68 illustrates how the spring 40 can be installed relative to the connecting member 60 so as to bias the connecting member towards rotating in a clockwise direction. As is shown, one end of the spring 40b can contact an inner surface of the bottom wall of the lower housing part 10 and another end 40c can contact the projection 70d.

FIGS. 50-53 show various views of the slide member 60. The slide member 60 can preferably be made as one-piece structure by e.g., injection molding. In this regard, it is preferably made of a plastic or synthetic resin such as, e.g., ABS plastic. The slide member 60 may also be made of ABS—red and have a finish designated as SPI-A2. Of course, other materials and/or finishes may be utilized, without leaving the scope of the invention. Additionally, by way of non-limiting example, the slide member 60 may have an overall length that is approximately 7.4 mm (measured horizontally across FIG. 50), and over width of approximately 5 mm (measured vertically in FIG. 50), and an overall thickness of approximately 2.4 mm. Moreover, the slide member 60 may even be made of a plurality of sections of parts which are joined together to form the complete slide member 60, without leaving the scope of the invention, although it is preferred that it be formed a one-piece member. It would be even more preferable if the slide member 60 were integrally formed with the lancet body, and in particular, integrally formed with the lower body part 10 and connected thereto with a living hinge (not shown).

As explained above, the slide member 60 has two generally parallel planar sides 60e which are designed to slidably engage with the inner surfaces 10d1 of the ribs 10d and a central opening 60a which is sized to receive therein the front projection 50h (thereby forming a snap connection) of the blade member 50. The generally planar surfaces 60b of the slide member 60 slidably engage upper surfaces 10d2 of the ribs 10d. An upper surface 60f of the slide member 60 contacts the lower surface 50f of the blade member 50 when the slide member 60 is snap connected to the blade member 50. This connection allows the slide member 60 to rotate relative to the projection 50h while ensuring that the slide member 60 cannot move axially relative to the blade member 50. Forward angled surfaces 60d of the slide member 60 are designed to frictionally slidably engage with angled surfaces 30b1 and 30c1 of the arms of the trigger cap 30 when the trigger cap 30 is in the initial pre-triggered position (see e.g., FIG. 24). Rear angled surfaces 60c of the slide member 60 are designed to frictionally engage with projections 30b2 and 30c2 of the arms 30b, 30c of the trigger cap 30 when the trigger cap 30 is in the post-triggered position (see e.g., FIG. 27).

FIGS. 54-58 show various views of the trigger cap 30. The trigger cap 30 can preferably be made as one-piece structure by e.g., injection molding. In this regard, it is preferably made of a plastic or synthetic resin such as, e.g., ABS plastic. The trigger cap 30 may also be made of ABS—red and have a finish designated as SPI-A2. Of course, other materials and/or finishes may be utilized, without leaving the scope of the invention. Additionally, by way of non-limiting example, the trigger cap 30 may have an overall length that is approximately 13.3 mm (measured from surface SCS to the ends of arms 30b and 30c), and over width of approximately 17.3 mm (measured across the shoulders 30a), and an overall thickness of approximately 4.2 mm. Moreover, the trigger cap 30 may even be made of a plurality of sections of parts which are joined together to form the complete trigger cap 30, without leaving the scope of the invention, although it is preferred that it be formed a one-piece member. It would be even more preferable if the trigger cap 30 were integrally formed with the lancet body, and in particular, integrally formed with the lower body part 1 and connected thereto with a living hinge (not shown).

As explained above, the trigger cap 30 has two generally parallel planar sides 30d and 30f. Upper surface 30d is designed to slidably engage with the upper surfaces 20h of the upper housing 20 and lower surface 30f is designed to slidably engage with upper surfaces 10d2 of the ribs 10d as well as upper surfaces of the ribs 10g. The generally parallel arms 30b, 30c include angled surfaces 30b1, 30c1 and inward facing projections 30b2, 30c2. The angled surfaces 30b1 and 30c1 are designed to frictionally slidably engage with angled surfaces 60d of the slide member 60 when the trigger cap 30 is in the initial pre-triggered position (see e.g., FIG. 24). Projections 30b2 and 30c2 of the arms 30b, 30c frictionally engage the rear angled surfaces 60c of the slide member 60 when the trigger cap 30 is in the post-triggered position (see e.g., FIG. 27). By way of non-limiting example, the blade receiving opening BO' can have a rectangular configuration as is shown in FIG. 54 with oppositely arranged circular openings sized to receive therein protruding members PM (see FIGS. 59-63). Other shapes are also contemplated for the opening BO'.

FIGS. 59-63 show various views of the protective cap PC'. The cap PC' can preferably be made as one-piece structure by e.g., injection molding. In this regard, it is preferably made of a plastic or synthetic resin such as, e.g., ABS plastic. The cap PC' may also be made of ABS—red and have a finish designated as SPI-A2. Of course, other materials and/or finishes may be utilized, without leaving the scope of the invention. Additionally, by way of non-limiting example, the cap PC' may have an overall thickness that is approximately 12.3 mm (measured horizontally in FIG. 61), and an overall width of approximately 13.6 mm (measured vertically in FIG. 61), and an overall length of approximately 21.7 mm (measured horizontally in FIG. 59). Moreover, the cap PC' may even be made of a plurality of sections of parts which are joined together to form the complete cap PC', without leaving the scope of the invention, although it is preferred that it be formed a one-piece member. It would be even more preferable if the cap PC' were integrally formed with the lancet body, and in particular, integrally formed with the lower body part 10 and connected thereto with a living hinge (not shown). As explained above, the cap PC' has generally parallel planar sides whose inner surfaces can include projections P which frictionally engage with recesses R of the body parts 20, 10.

All the parts of the lancet device, with the exception of the springs (which can be made of spring steel) and with the exception of the lancet blade member/blade tip, may be made from plastic materials and can be formed using conventional injection molding techniques or other known manufacturing methods. However, when practical, other materials and manufacturing processes may also be utilized.

It is noted that the foregoing examples have been provided merely for the purpose of explanation and are in no way to be construed as limiting of the present invention. While the present invention has been described with reference to exemplary embodiments, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A single-use blade lancet device, comprising:
    a body;
    a triggering mechanism;
    a pivotally mounted connecting member comprising:
        a projection which extends into an opening of a mounting projection arranged within the body;
    a blade member movably mounted within the body and comprising:
        a front end having a blade tip and being arranged on the blade member;
    the blade member being movable at least between a first retracted position, an extended position, and a second retracted position;
    the connecting member being pivotally connected to the blade member via a first projection and an opening;
    a second projection arranged in the body and moving with the blade member; and
    a torsion spring mounted to the mounting projection and being configured to move the connecting member during a triggering of the device, whereby the blade member is caused to move from the first retracted position towards the extended position and then towards the second retracted position,
    wherein, when the single-use blade lancet device is triggered, the first projection moves along a curved path, the second projection moves along a linear path, and the blade tip experiences pivotal movement about an axis of the second projection.

2. The device of claim 1, further comprising a removable device for preventing triggering of the device.

3. The device of claim 1, wherein the body comprises a two-piece body.

4. A method of using the device of claim 1, the method comprising:
    removing a removable safety device or cap from the body; and
    triggering the device to cause movement of the blade member.

5. A single-use blade lancet device, comprising:
    a two-piece body;
    a triggering mechanism;
    a removable device for preventing triggering of the device;
    a pivotally mounted connecting member;
    a blade member movably mounted within the body and comprising:
        a front end having a blade tip and being arranged on the blade member;
    the blade member being movable at least between a first retracted position, an extended position, and a second retracted position;
    the connecting member being pivotally connected to the blade member via a first projection and an opening;
    the connecting member being pivotally connected to a mounting projection arranged within the body via another projection and another opening;
    a second projection arranged in the body and moving with the blade member; and
    a torsion spring mounted to the mounting projection and being configured to move the connecting member during a triggering of the device, whereby the blade member is caused to move from the first retracted position towards the extended position and then towards the second retracted position,
    wherein, when the single-use blade lancet device is triggered, the first projection moves along a curved oath, the second projection moves and is guided linearly, and the blade tip experiences pivotal movement about an axis of the second projection.

6. A method of using the device of claim 5, the method comprising:
    removing a removable safety device or cap from the body; and
    triggering the device to cause movement of the blade member.

7. A single-use blade lancet device, comprising:
    a two-piece body;
    a triggering mechanism;
    a connecting member comprising:
        a projection which extends into an opening of a mounting projection;

a blade member comprising:
  a front end having a blade tip and being arranged on the blade member;
the blade member being movable at least between a first retracted position, an extended position, and a second retracted position;
the connecting member being pivotally connected to the blade member via a first projection and an opening;
a second projection arranged in the body and moving with the blade member; and
a torsion spring mounted to the mounting projection and being configured to move the connecting member during a triggering of the device, whereby the blade member is caused to move from the first retracted position towards the extended position and then towards the second retracted position,
wherein, when the single-use blade lancet device is triggered, the first projection moves along a curved oath, the second projection is guided along a linear oath, and the blade tip experiences pivotal movement about an axis of the second projection.

8. A method of using the device of claim 7, the method comprising:
removing a removable safety device or cap from the body; and
triggering the device to cause movement of the blade member.

* * * * *

UNITED STATES PATENT AND TRADEMARK OFFICE
CERTIFICATE OF CORRECTION

| | | |
|---|---|---|
| PATENT NO. | : 7,704,265 B2 | Page 1 of 1 |
| APPLICATION NO. | : 11/265151 | |
| DATED | : April 27, 2010 | |
| INVENTOR(S) | : Schraga | |

It is certified that error appears in the above-identified patent and that said Letters Patent is hereby corrected as shown below:

Title Page, Item (56), Other Publications add --Office Action for Chinese Application No. 20060040348.7--

Title Page, Item (56), Other Publications add --English Translation of Office Action for Chinese Application No. 20060040348.7--

On Column 24, line 52 (Claim 5, line 27) of the printed patent, "oath" should be --path--

On Column 26, line 4 (Claim 7, line 24) of the printed patent "oath" should be --path--

On Column 26, line 5 (Claim 7, line 25) of the printed patent "oath" should be --path--

Signed and Sealed this

Fourteenth Day of December, 2010

David J. Kappos
*Director of the United States Patent and Trademark Office*